US007135143B2

(12) United States Patent
Abbott et al.

(10) Patent No.: US 7,135,143 B2
(45) Date of Patent: Nov. 14, 2006

(54) DETECTING COMPOUNDS WITH LIQUID CRYSTALS

(75) Inventors: Nicholas L. Abbott, Madison, WI (US); Rahul R. Shah, St. Paul, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 660 days.

(21) Appl. No.: 09/931,635

(22) Filed: Aug. 16, 2001

(65) Prior Publication Data

US 2002/0164604 A1 Nov. 7, 2002

Related U.S. Application Data

(60) Provisional application No. 60/275,752, filed on Mar. 14, 2001.

(51) Int. Cl.
G01N 21/29 (2006.01)
(52) U.S. Cl. .................. 422/82.05; 422/55; 422/68.01; 422/82.01; 436/4; 436/501; 436/524; 436/528; 436/805; 427/162; 349/199
(58) Field of Classification Search ............ 422/82.05, 422/55, 57, 68.01, 82.01; 436/4, 501, 524, 436/528, 805; 427/162; 349/199
See application file for complete search history.

(56) References Cited

U.S. PATENT DOCUMENTS

| 5,620,850 A | 4/1997 | Bamdad et al. |
| 6,284,197 B1 | 9/2001 | Abbott et al. |
| 6,288,392 B1 | 9/2001 | Abbott et al. |

FOREIGN PATENT DOCUMENTS

| WO | WO 99/63329 | 12/1999 |
| WO | WO 99/64862 | 12/1999 |

OTHER PUBLICATIONS

Fergason, J., "Liquid Crystals," *J. Sci. Amer.*, vol. 211, pp. 77-83, 1964.
Fergason, J., et al., "Thermal Radiography Utilizing Liquid Crystals," *Mol. Cryst. Liq. Cryst.*, vol. 13, pp. 149-164, 1971; published by Gordon and Breach Science Publishers.
Novak, T. J., et al., "Use of Anisotropic Materials as Chemical Detectors," *Analytical Letters*, vol. 5, No. 3, pp. 187-192, 1972; Marcel Dekker, Inc.
Poziomek, E. J., et al., "Use of Liquid Crystals as Vapor Detectors," *Mol. Cryst. Liq. Cryst.*, vol. 27, pp. 175-185, 1973; published by Gordon and Breach Science Publishers, Ltd.
Kolesar, Jr., E., "Organophosphorus Compound Detection with a Supported Copper + Cuprous Oxide Island Film. 1. Gas-Sensitive Gilm Physical characteristics and Direct Current Studies," *Anal. Chem.*, vol. 60, No. 17, pp. 1731-1736, Sep. 1, 1988.

(Continued)

*Primary Examiner*—Monique T. Cole
(74) *Attorney, Agent, or Firm*—Foley & Lardner LLP

(57) ABSTRACT

A device for detecting a compound in a sample includes a substrate and a self-assembled monolayer. The substrate includes a support with a metallized top surface, and the self-assembled monolayer includes an alkanethiol attached to the metallized top surface of the substrate and having a functional group that reversibly or irreversibly interacts with the compound. A liquid crystal is disposed on the self-assembled monolayer opposite the side of the self-assembled monolayer attached to the metallized top surface of the substrate. The liquid crystal includes a moiety that interacts with the functional group of the alkanethiol. When the compound is present in a sample that that contacts the self-assembled monolayer, the orientation of the liquid crystal is altered.

67 Claims, 10 Drawing Sheets

OTHER PUBLICATIONS

Kolesar, Jr., E., et al., "Organophosphorus Compound Detection with a Supported Copper + Cuprous Oxide island Film. 2. Alternating Current Studies and Sensor Performance," *Anal. Chem.*, vol. 60, No. 17, pp. 1737-1743, Sep. 1, 1988.

Pieranski, P., et al., "Adsorption-induced anchoring transistions at nematic-liquid-crystal-crystal interfaces," *Physical Review A*, vol. 40, No. 1, pp. 317-322, Jul. 1, 1989; published by The American Physical Society.

Nuzzo, R. G., et al., "Fundamental Studies of Microscopic Wetting on Organic Surfaces. 1. Formation and Structural characterization of a Self-Consistent Series of Polyfunctional Organic Monolayers," *J. Am. Chem. Soc.*, vol. 112, pp. 558-569, 1990.

Bechhoefer, J., et al., "Systematic Studies of the Anchoring Transition in Nematic Liquid Crystals," *Physical Review A*, vol. 41, No. 6, pp. 3187-3191, Mar. 15, 1990; published by The American Physical Society.

Pieranski, P., et al., "Adsorption-Induced Anchoring Transitions," *Mol. Cryst. Liq. Cryst.*, vol. 179, pp. 285-315, 1990; published by Gordon and Breach Science Publishers S.A., printed in the United States of America.

Bechhoefer, J., et al., "Anchoring Transitions of Nematic Liquid Crystals," *Phase Trans.*, vol. 33, pp. 227-236, 1991; published by Gordon and Breach Science Publishers S.A., printed in the United Kingdom.

Kepley, L. J., et al., "Selective Surface Acoustic Wave-Based Organophosphonate Chemical Sensor Employing a Self-Assembled Composite Monolayer: A New Paradigm for Sensor Design," *Anal. Chem.*, vol. 64, pp. 3191-3193, Dec. 15, 1992.

Butler, M. A., et al., "Fiber Optic Micromirror Studies of the Interaction of Thin Copper Films with an Organophosphonate," *Anal. Chem.*, vol. 64, No. 17, pp. 1851-1854, Sep. 1, 1992.

Milanko, O. S., et al., "Evaluation of coating materials used on piezoelectric sensors for the detection of organophosphorus compounds in the vapour phase," *Anal. Chim. Acta*, vol. 269, pp. 289-300, 1992; published by Elsevier Science Publishers B.V.

Jerome, B., et al., "Anchoring of nematic liquid crystals on mica in the presence of volatile molecules," *Physical Review E*, vol. 48, No. 6, pp. 4556-4574, Dec. 1993; published by The American Physical Society.

Yao, S., et al., "Circuit network analysis method applied to surface acoustic wave impedance system in liquids," *Anal. Chim. Acta*, vol. 294, pp. 311-318, 1994; published by Elsevier Science Publishers B.V.

Drawhorn, R. A., et al., "Anchoring of Nematic Liquid Crystals on Self-Assembled Monolayers Formed from Alkanethiols on Semi-transparent Films of Gold," *J. Phys. Chem.*, vol. 99, No. 45, pp. 16511-16515, 1995.

Yang, L., et al., "Chemical Sensing Using Sol-Gel Derived Planar Waveguides and Indicator Phases," *Anal. Chem.*, vol. 67, No. 8, pp. 1307-1314, Apr. 15, 1995; published by American Chemical Society.

Gupta, V. K., et al., "Azimuthal anchoring transition of nematic liquid crystals on self-assembled monolayers formed from odd and evan alkanethiols," *Physical Review E*, vol. 54, No. 5, pp. R4540-R4543, Nov. 1996; published by The American Physical Society.

Gupta, V. K., et al., "Uniform Anchoring of Nematic Liquid Crystals on Self-Assembled Monolayers Formed from Alkanethiols on Obliquely Deposited Films of Gold," *Langmuir*, vol. 12, No. 10, pp. 2587-2593, 1996; published by American Chemical Society.

Yang, H. C., et al., "Molecular Interactions between Organized, Surface-Confined Monolayers and Vapor-Phase Probe Molecules. 8. Reactions between Acid-Terminated Self-Assembled Monolayers and Vapor-Phase Bases," *Langmuir*, vol. 12, No. 3, pp. 726-735, 1996; published by American Chemical Society.

Wells., M., et al., "Interactions between Organized, Surface-Confined Monolayers and Vapor-Phase Probe Molecules. 9. Structure/Reactivity Relationship between Three Surface-Confined Isomers of Mercaptobenzoic Acid and Vapor-Phase Decylamine," *Langmuir*, vol. 12, No. 8, pp. 1989-1996, 1996.

Crooks, R. M., "Interactions between self-assembled monolayers and an organosphosphonate," *Faraday Discuss.*, vol. 107, pp. 285-305, 1997.

Delamarche, E., et al., "Patterned Delivery of Immunoglobulins to Surfaces Using Microfluidic Networks," *Science*, vol. 276, pp. 779-781, May 2, 1997.

Jenkins, A. L., et al., "Polymer Based Lanthanide Luminescent Sensors for the Detection of Nerve Agents," *Anal. Comm.*, vol. 34, pp. 221-224, Aug. 1997.

Gupta, V. K., et al., "Optical Amplification of Ligand-Receptor Binding Using Liquid Crystals," *Science*, vol. 279, pp. 2077-2080, Mar. 27, 1998.

Ricco, A. J., et al., "Surface Acoustic Wave Chemical Sensor Arrays: New Chemically Sensitive Interfaces Combined with Novel Cluster Analysis To Detect Volatile Organic Compounds and Mixtures," *Acc. Chem. Res.*, vol. 31, No. 5, pp. 289-296, 1998; published by American Chemical Society.

Crooks, R. M., et al., "New Organic Materials Suitable for Use in Chemical Sensor Arrays," *Acc. Chem. Res.*, vol. 31, No. 5, pp. 219-227, 1998; published by American Chemical Society.

Swager, T. M., "The Molecular Wire Approach to Sensory Signal Amplification," *Acc. Chem. Res.*, vol. 31, No. 5, pp. 201-207, 1998; published by American Chemical Society.

Shah, R. R., et al., Using Liquid Crystals To Image Reactants and Products of Acid-Base Reactions on Surfaces with Micrometer Resolution, *J. Am. Chem. Soc.*, vol. 121, No. 49, pp. 11300-11310, 1999; published by American Chemical Society.

Skaife, J. J., et al., "Quantitative Characterization of Obliquely Deposited Substrates of Gold by Atomic Force Microscopy: Influence of Substrate Topography on Anchoring of Liquid Crystals," *Chem. Mater.*, vol. 11, No. 3, pp. 612-623, 1999; published by American Chemical Society.

Bertilsson, L., et al., "On the Adsorption of Dimethyl Methylphosphonate on Self-Assembled Alkanethiolate Monolayers: Influence of Humidity," *Langmuir*, vol. 15, No. 4, pp. 1128-1135, 1999; published by American Chemical Society.

Jenkins, A. L., et al., "Polymer-Based Lanthanide Luminescent Sensor for Detection of the Hydrolysis Product of the Nerve Agent Soman in Water," *Anal. Chem.*, vol. 71, No. 2, pp. 373-378, Jan. 15, 1999; published by American Chemical Society.

Niculescu, M., et al., "Redox Hydrogel-Based Amperometric Bienzyme Electrodes for Fish Freshness Monitoring," *Anal. Chem.*, vol. 72, No. 7, pp. 1591-1597, Apr. 1, 2000; published by American Chemical Society.

Shah, R. R., et al., "Coupling of the Orientations of Liquid Crystals to Electrical Double Layers formed by the Dissociation of Surface-Immobilized Salts," *J. Phys. Chem.*, vol. 105, No. 21, pp. 4936-4950, 2001; published by American Chemical Society.

DETECTING COMPOUNDS WITH LIQUID CRYSTALS

CROSS-REFERENCES TO RELATED APPLICATIONS

This application claims priority to U.S. Provisional Application No. 60/275,752, filed Mar. 14, 2001, the entire disclosure of which is incorporated herein.

GOVERNMENT RIGHTS

This invention was made with United States government support awarded by the following agency: NAVY N00014-99-1-0250. The United States has certain rights in this invention.

FIELD OF THE INVENTION

The invention relates generally to methods and devices for detecting compounds in samples. More particularly, the invention relates to methods and devices for detecting compounds with liquid crystals based on reversible or nonreversible interactions between compounds and functional groups on a surface that can detect such interactions.

BACKGROUND OF THE INVENTION

The ability to detect the presence of compounds in samples is extremely important in commerce and everyday life. The field of analytical chemistry has thus seen continuous development in this area. Although various methods have been developed that allow for the detection of various target species in samples taken from sources such as the environment, a continuing need remains for devices and methods for detecting such compounds.

While certain methods have been developed for the detection of organoamines and organophosphorus compounds, a need remains for methods which do not require expensive instrumentation and which are both convenient and easy to use. Organophosphorus compounds such as organophosphonates are known to destroy nerve impulse transmissions between nerve fibers, muscles, and glands within mammals and insects. Therefore, these compounds have been utilized as nerve agents for chemical warfare and as pesticides in commercial agricultural applications. The toxicity of many of these materials, as measured by the $LD_{50}$ value, from inhalation into the lungs of the most common such chemical warfare agents is around 200 ppbv. Furthermore, organophosphonates may be delivered through a variety of routes including by absorption through the skin, by injection into a vein, by injection under the skin, and by oral delivery. The exposure criteria for many pesticides and insecticides is less clear because a wide variety of organophosphonates have been synthesized. Conventionally, exposure of agricultural workers to organophosphonates is conducted using body fluids because measurements of vapor concentrations of these materials remains difficult. Therefore, occupational monitoring of these compounds has focused on measuring the enzymatic activity of cholinesterase in blood samples, by analyzing metabolite byproducts in urine samples, and by analyzing saliva or perspiration.

Past studies for detecting organophosphonates have employed a wide range of coating materials and schemes for transducing physical changes in the states of the coatings. These schemes include: optical techniques that use fiber-optic micromirrors and waveguides; electrical resistivity methods; mass-sensitive methods such as quartz crystal microbalances and surface acoustic wave devices; cantilever sensors that deflect upon absorption of analyte; lanthanide ions that luminesce upon coordination of the organophosphonate with the copolymer; and surface analytical techniques such as infrared spectroscopy. M. A. Butler, A. J. Ricco, *Anal. Chem.*, 1992, 64, 1851; J. F. Giuliani, N. L. Jarvis, A. Snow, *ACS Symposium Series No.* 309., 1986, 320; M. Eldefrawi, K. Rogers, A. Eldefrawi, *Pesticides and the Future: Toxicological Studies of Risks and Benefits, Reviews in Pesticides Toxicology* 1, edited by Hodgson, E., Roe, R. M., Motoyama, N., Department of Toxicology, University of North Carolina, Raleigh, 1991; E. S. Kolesar Jr., R. M. Walser, *Anal. Chem.*, 1988, 60, 1731; E. S. Kolesar Jr., R. M. Walser, *Anal. Chem.*, 1988, 60, 1737; S. W. Oh, Y. H. Kim, D. J. Yoo, S. M. Oh, S. J. Park, *Sensors Actuat B.*, 1993, 13–14, 400; O. S. Milanko, S. A. Milinkovic, L. V. Rajakovic, *Anal. Chim. Acta.*, 1992, 269, 289; W. P. Carey, B. R. Kowalski, *Anal. Chem.*, 1986, 50, 3077; M. S. Nieuwenhuizen, J. L. N. Hartveld, *Sensors Actuat B.*, 1994, 18–19, 502; M. S. Nieuwenhuizen, J. L. N. Hartveld, *Talanta.*, 1994, 41, 461; J. W. Grate, S. N. Kaganove, S. J. Patrash, R. Craig, M. Bliss, *Chem. Mater.*, 1997, 9, 1201; L. Bertilsson, K. Potje-Kamloth, H.-D. Liess, B. Leidberg, *Langmuir* 1999, 15, 1128; G. Li, L. W. Burggraf, *Appl. Phys. Lett.*, 2000, 76, 1122; A. L. Jenkins, O. M. Uy, G. M. Murray, *Anal. Comm.*, 1997, 34, 221; and A. L. Jenkins, O. M. Uy, G. M. Murray, G. M. *Anal. Chem.*, 1999, 71, 373.

The detection of biogenic amines is important because these compounds are markers of the freshness of foods such as fish and meat. Common biogenic amines such as histamine, putrescine, and cadaverine are produced by the microbial decarboxylation of the amino acids histidine, ornithine, and lysine, respectively. In order to provide a fresh and safe food supply, governments such as the United States have placed maximum limits for these materials in foods. A convenient and simple method for detecting these compounds is thus an important problem that has not yet been resolved.

Past studies of the binding of low molecular weight compounds such as amines to receptors hosted on surfaces have employed one of three general transduction schemes: optical techniques that utilize fluorescence, chemiluminescence or waveguide/surface plasmon resonance; electrical methods utilizing potentiometric, amperometric, and conductive techniques; and mass-sensitive methods such as quartz crystal microbalance and surface acoustic wave devices. T. M. Swager, *Acc. Chem. Res.*, 1998, 31, 201; E. Delamarche, A. Bernard, H. Schmid, B Michel, J. A. Biebuyck, *Science*, 1997, 276, 779; E. V. Groman, J. M. Rothenberg, E. A. Bayer, M. Wichek, *Methods Enzymol.*, 1990, 184, 208–217; L. Yang, S. S. Saavedra *Anal. Chem.*, 1995, 67, 1307; L. S. Jung, C. T. Campbel, T. M. Chinowsky, M. N. Mar, S. S. Yee, *Langmuir,* 1998, 14, 5636; R. P. Buck, E. Lindner, *Acc. Chem. Res.*, 1998, 31, 257; M. Niculescu, C. Nistor, I. Frébort, P. Pe, B. Mattiasson, E Csöregi, *Anal. Chem.*, 2000, 72, 1591; J. Wang, Q. Chen, C. L. Renschler, C. White, *Anal. Chem.*, 1994, 66: 1988; H. Bayley, C. R. Martin, *Chem. Rev.*, 2000, 100, 2575; C Barnes, C. D'Silva, J. P. Jones, T. J. Lewis, *Sensors and Actuators A*, 1992, 31, 159; M. Rodahl, F. Hoeoek, B. Kasemo, *Anal. Chem.*, 1996, 68, 2219; S. Yao, K. Chen, D. Liu, L. Nie, *Anal. Chim. Acta.*, 1994, 294, 311; J. W. Grate, *Chem. Rev.*, 2000, 100, 2627; and S. J. Martin, G. C. Frye, S. D. Senturia, *Anal. Chem.*, 1994, 66, 2201.

Although many of the conventional assay methods work well in detecting the presence of target species, most conventional assay methods are expensive and often require instrumentation and highly trained individuals, which makes them difficult to use routinely in the field. For example, the detection of analytes using fluorescence or chemiluminescence techniques requires the use of labels while electrical, mass-sensitive, and surface plasmon techniques require complex instrumentation. Thus, a continuing need exists for assay devices and systems which are easier to use, which do not require complex instrumentation, and which allow for evaluation of samples in remote locations where quick results may be required.

Recently, assay devices that employ liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B., Abbott N. L. Science, 279, (1998), pp. 2077–2079. In addition, PCT publication WO 99/63329 published on Dec. 9, 1999, discloses assay devices using SAMs attached to a substrate and liquid crystal layer that is anchored by the SAM.

Although various methods have been used to detect the presence of a compound in a sample, a continuing unmet need exists for a simple device and method that may be used to rapidly detect the presence of a compound in liquid or gaseous samples. A continuing need also remains for a method of manufacturing a device for use in detecting the presence of compounds in a sample.

SUMMARY OF THE INVENTION

The present invention provides devices and methods for detecting the presence of a compound in a sample. The invention also provides optical cells and kits for employment in detecting the presence of a compound in a sample.

A device for detecting the presence of a compound in a sample is provided. The device includes a substrate, a self-assembled monolayer, and a liquid crystal. The substrate of the device includes a support with a metallized top surface, and the self-assembled monolayer includes an alkanethiol attached to the metallized top surface of the substrate. The alkanethiol of the device includes a functional group that reversibly or irreversibly binds or interacts with the compound. The liquid crystal is disposed on a top surface of the self-assembled monolayer opposite the side of the self-assembled monolayer attached to the metallized top surface of the substrate, and the liquid crystal includes a moiety that interacts with the functional group of the alkanethiol. When the compound is present in a sample that contacts the self-assembled monolayer, the orientation of the liquid crystal disposed on the self-assembled monolayer is altered.

The invention also provides devices in which the functional group of the alkanethiol of the device includes a functional group selected from a carboxylic acid or a metal carboxylate. In other devices, the functional group is a carboxylic acid whereas in still other devices the functional group of the alkanethiol is a metal ion complex such as a metal carboxylate formed from a metal ion and a carboxylic acid group on the alkanethiol. In yet other devices, the functional group on the alkanethiol is a copper carboxylate group, more preferably a $Cu^{+2}$ carboxylate.

Devices are also provided in which the liquid crystal is a nematic liquid crystal. In yet other devices, the liquid crystal includes a nitrile group, and the functional group of the alkanethiol is a carboxylic acid or a metal carboxylate. In still other provided devices, the liquid crystal is 4-cyano-4'-pentylbiphenyl.

Devices are also provided in which the alkanethiol has the formula $HS(CH_2)_nCO_2H$ and n is an integer selected from the group consisting of 1 2, 3, 4, 5, 6, 7, 8, 9, 10, 11, 12, 13, 14, 15, 16, 17, 18, 19, and 20. In other devices, n is 10.

Other devices are provided in which the metallized top surface of the substrate includes a metal selected from gold or silver whereas in other devices the metal is gold. In some devices, the gold is obliquely deposited at an angle of from about 30° to about 60 to a top surface of the support. In still other devices, gold is obliquely deposited at an angle of about 50° to the top surface of the support. In still other such devices, the gold is deposited over a layer of an adhesion promoting material such as titanium. In still other devices, the support is a glass plate or a glass slide.

Devices are provided in which the uniformity in the orientation of the liquid crystal on the top surface of the self-assembled monolayer increases when the self-assembled monolayer is exposed to the sample and the sample includes the compound. Yet other devices are provided in which the uniformity in the orientation of the liquid crystal on the top surface of the self-assembled monolayer decreases when the self-assembled monolayer is exposed to the sample and the sample includes the compound.

Optical cells are also provided. Optical cells include a device for detecting the presence of a compound in a sample having any of the characteristics described above and a second surface that uniformly aligns the liquid crystal when the liquid crystal contacts the second surface. The second surface contacts a first surface of the liquid crystal which is opposite a second surface of the liquid crystal that contacts the self-assembled monolayer of the device.

Optical cells are provided in which the second surface that uniformly aligns the liquid crystal is a rubbed surface. Still other optical cells are provided in which the second surface that uniformly aligns the liquid crystal is a second self-assembled monolayer on a second metallized surface of a second support. Still other optical cells are provided in which the optical cell defines a space between the top surface of the self-assembled monolayer of the device and the second surface that uniformly aligns the liquid crystal.

Methods for detecting the presence of a compound in a sample are also provided. A method for detecting the presence of a compound in a sample includes contacting a device for detecting the presence of a compound in a sample with the sample where the device includes a substrate that includes a support having a metallized top surface and a self-assembled monolayer. The self-assembled monolayer includes an alkanethiol attached to the metallized top surface of the metallized top surface of the substrate, and the alkanethiol includes a functional group that reversibly or irreversibly interacts with the compound. The method further includes disposing a liquid crystal on a top surface of the self-assembled monolayer of the substrate and determining whether the orientation of the liquid crystal on the self-assembled monolayer changes after the device contacts the sample. The liquid crystal has a moiety that interacts with the functional group of the alkanethiol of the self-assembled monolayer.

Methods are further provided in which the liquid crystal is disposed on the surface of the self-assembled monolayer of the substrate after the device contacts the sample whereas other methods are provided in which the liquid crystal is disposed on the surface of the self-assembled monolayer before the device contacts the sample.

Still other methods are provided in which the functional group of the alkanethiol and the alkanethiol have any of the characteristics described above with respect to the device for detecting the presence of a compound in a sample.

Still other methods are provided in which the liquid crystal has any of the characteristics described above with respect to the device for detecting the presence of a compound in a sample.

Still other methods are provided in which the metallized top surface of the device has any of the characteristics described above with respect to the device for detecting the presence of a compound in a sample.

Still other methods are provided in which the support is a glass plate or a glass slide.

Methods for detecting the presence of a compound in a sample are provided in which the uniformity in the orientation of the liquid crystal disposed on the self-assembled monolayer increases after the device is contacted with the sample when the sample includes the compound.

Still other methods are provided in which the device for detecting the presence of a compound in a sample is a component of an optical cell that includes a second surface that uniformly aligns the liquid crystal when the liquid crystal contacts the second surface.

In still other provided methods and devices, the compound that the functional group of the alkanethiol interacts with is an amine such as an alkylamine. Still other methods are provided in which the alkylamine has the formula $H_2N(CH_2)_mCH_3$, wherein m has a value of 0, 1, 2, 3, 4, 5, 6, 7, 8, 9, or 10. In yet other methods and devices, m has a value of 5 such that the alkylamine is hexyl amine. Still other methods and devices are provided in which the amine is a biogenic amine such as putrescine, cadaverine, or histamine.

In still other provided methods and devices, the compound that the functional group of the alkanethiol interacts with is a phosphorus compound.

In still other methods and devices, the compound that the functional group of the alkanethiol interacts with is an organophosphonate such as a dialkyl alkylphosphonate such as dimethyl methylphosphonate.

Still further methods and devices are provided in which the sample is a gaseous sample such as the gas in a room or outdoor environment whereas in other methods and devices, the sample is a liquid sample.

Kits for detecting the presence of a compound in a sample are also provided. Kits for detecting the presence of a compound in a sample include a substrate having a support with a metallized top surface; an alkanethiol having a functional group that reversibly or irreversibly interacts with the compound; and a liquid crystal having a moiety that interacts with the functional group of the alkanethiol.

Still further kits are provided wherein the alkanethiol is attached to the metallized top surface of the substrate. Still other provided kits include instructions for detecting the presence of a compound whereas in further provided kits, the functional group of the alkanethiol includes a carboxylic acid or a metal carboxylate functional group.

Kits are further provided in which the liquid crystal, alkanethiol, substrate, and/or metallized top surface have any of the characteristics set forth above with respect to the device for detecting the presence of a compound in a sample.

A method for manufacturing a device for detecting the presence of a compound is still further provided. The method includes depositing a metal on a surface of a support to form a support with a metallized surface; contacting an alkanethiol with the metallized surface of the support to form a self-assembled monolayer with a bottom surface attached to the metallized top surface of the support and a top surface; and depositing a liquid crystal on the top surface of the self-assembled monolayer. The alkanethiol includes a functional group that reversibly or irreversibly interacts with the compound, and the liquid crystal includes a moiety that interacts with the functional group of the alkanethiol.

Other methods for manufacturing a device for detecting the presence of a compound in a sample are provided in which the contacting of the alkanethiol with the metallized surface of the support includes contacting a carboxylic acid on the alkanethiol with a metal salt such as a copper salt to provide a metal carboxylate such as a $Cu^{+2}$ carboxylate.

Still other methods for manufacturing a device for detecting the presence of a compound are provided which include positioning a second surface above the top surface of the self-assembled monolayer. In such methods, the second surface preferably uniformly aligns the liquid crystal when the liquid crystal contacts the second surface. In still other such methods the second surface is a second support that includes a metallized surface that has a second self-assembled monolayer on it that includes a second alkanethiol. In some such methods the second alkanethiol is different from the alkanethiol having the functional group that interacts with the compound.

Still further methods for manufacturing a device for detecting the presence of a compound in a sample are provided in which the alkanethiol, the functional group of the alkanethiol, the liquid crystal, the support, and/or the metallized top surface of the support having any of the features described above with respect to the device for detecting the presence of a compound in a sample.

Further methods for manufacturing a device for detecting the presence of compounds in a sample are provided in which the compound to be detected has any of the features described above.

Further objects, features and advantages of the invention will be apparent from the following detailed description when taken in conjunction with the accompanying drawings.

DETAILED DESCRIPTION OF THE INVENTION

Figure 1A:
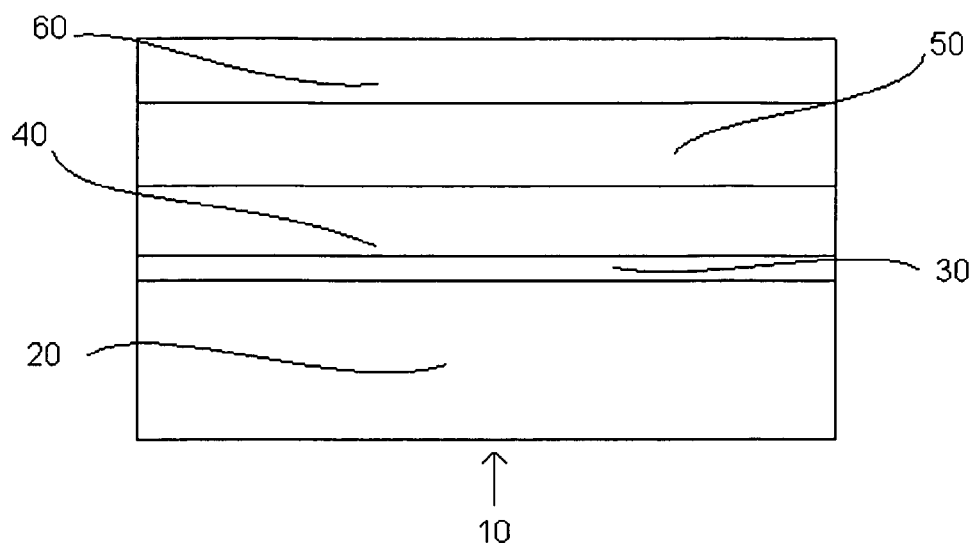
FIGS. 1A and B are schematic diagrams of cross sections of preferred devices for detecting the presence of a compound in a sample.

Generally, the invention provides devices, optical cells, kits, and methods for detecting the presence of a compound in a sample. The invention also generally provides methods for preparing devices and optical cells for detecting the presence of a compound in a sample.

All ranges recited herein include all combinations and subcombinations included within that range's limits. For example, a deposition angle of from about 30° to about 60° includes ranges of from 30° to 60°, of from 35° to 55°, of from 40° to 52°, of from 50° to 60, and angles of about 50°, of 50°, of about 45°, and of about 55° etc.

Some of the characteristics which a suitable device for detecting compounds should possess generally include: a surface with a functional group that reversibly or irreversibly interacts with the compound to be detected and a liquid crystal that includes a moiety which reversibly interacts with the functional group of the surface. The liquid crystal is typically deposited over the surface with the functional group that interacts with the compound, and the interaction of the moiety of the liquid crystal with the functional group of the surface is preferably weaker than the interaction between the compound and the functional group such that the liquid crystal is competitively displaced by the compound leading to a visually detectable change in the orientation of the liquid crystal on the surface.

The surface with the functional group that interacts with the compound and moiety of the liquid crystal may take various forms. In one preferred embodiment, the surface is a self-assembled monolayer (SAM) formed from a thiol that includes the functional group that interacts with the compound to be detected, and the surface overlies a metallized top surface of a substrate that includes a support. However, this is not required in the devices and optical cells used to detect the compounds in a sample. Other preferred devices for detecting the presence of a compound include a surface with functional groups that comprises a semiconductor-based material with a self-assembled monolayer overlying it that includes the functional groups. The self assembled monolayer in preferred such devices is an alkanethiol that bears the functional group. Gallium arsenide is an example of one preferred semiconductor material that may be used in such a device, although any other suitable semiconductor material that forms self-assembled monolayers known to those skilled in the art may also be employed. Thus, many different types of surface with functional groups may be utilized in devices for detecting the presence of a compound. For example, surfaces with functional groups may comprise polymeric surfaces with functional groups that interact with the compound or a portion of the compound and the moiety of the liquid crystal. Displacement of the liquid crystal from the functional group by the compound when it is present produces the change in the orientation of the liquid crystal which is visualized indicating the presence of the compound. Suitable surfaces with functional groups include, but are not limited to, the preferred SAM formed from an alkanethiol or other thiol with a functional group that interacts with the compound as described above; polymers with the functional groups; rubbed surfaces with the functional groups; and inorganic surfaces, such as, but not limited to those formed from silica that have been contacted with solutions of metal ions such that ion exchange leads to the incorporation of a desired metal ion onto the surface of the glass. In some cases the inorganic surfaces can be obliquely deposited.

Generally, the surface including the functional groups that interact with the compound overlays a support forming a substrate. A wide variety of materials may be used as supports in the devices and methods of the present invention as will be apparent to those skilled in the art. Preferred supports include polymers and silica-containing materials such as glass and quartz. Examples of polymeric supports include, but are not limited to, polystyrene, polycarbonates, and polymethyl methacrylate. Other materials suitable for use as supports include metal oxides such as, but not limited to, indium oxide, tin oxide, and magnesium oxide and metals such as, but not limited to, gold, silver, and platinum. Still other materials that may be used as supports include cellulosic materials such as nitrocellulose, wood, paper, and cardboard, and sol-gel materials. Especially preferred supports include glass, quartz, and silica, and most preferred supports include glass slides, glass plates, and silica wafers. Preferably, such supports are cleaned prior to use. For example, glass slides and plates may be cleaned by treatment in "piranha solution" (70% $H_2SO_4$/30% $H_2O_2$) for 1 hour and then rinsed with deionized water before drying under a stream of nitrogen. "Piranha solution" requires care in handling as it reacts violently with organic compounds and should not be stored in closed containers.

A preferred substrate for use in accordance with the present invention contains a top surface with a layer of obliquely deposited metal on it, although various methods known to those skilled in the art may be used to prepare a metallized top surface. Such methods include, but are not limited to, evaporation to form a uniformly deposited metal surface, sputtering, and electrodeless deposition. Metals that may be used include, but are not limited to gold, silver, copper, platinum, and palladium. Preferred metals include gold and silver with gold being especially preferred. Typically, an obliquely deposited gold or silver surface will overlay a surface of titanium or another adhesion promoting material which has already been deposited on a top surface of the support. The use of the titanium provides better adhesion of the obliquely deposited silver, or more preferably gold in preparing the metallized surface. However, use of titanium or another adhesion-promoting material is not required as suitable detection surfaces and devices may be prepared without the use of such materials. If an adhesion promoting material is used, a layer of varying thickness may be applied to the underlying support. In preferred embodiments, approximately 10 Å of Ti is deposited on a support such as a glass slide or plate. In other preferred embodiments, the amount of adhesion-promoting material ranges from 5 Å to 1000 Å, from 5 Å to 20 Å, and more preferably from 8 Å to 15 Å. Other adhesion promoting materials include chromium. Because chromium is mobile in gold, titanium is sometimes preferred over chromium when preparing thin films of gold. Still another type of adhesion promoter is an organic layer formed from a compound such as, but not limited to, mercaptopropyltrimethoxysilane.

In more preferred embodiments, a layer of an obliquely deposited metal, preferably gold, is deposited on a cleaned surface of the support by evaporating it at a rate of about 0.2 Å/s at a pressure of less than or about $5\times10^{-6}$ torr. See Gupta, V. K. et al. Chemistry of Materials, 8, (1996), p. 1366. In other preferred embodiments, a metal such as gold is deposited on a top surface of a support that contains an adhesion-promoting material such as titanium. The layer of a metal such as gold on the metallized surface of the support typically ranges from at or about 30 Å to at or about 500 Å, or more preferably from 50 Å to 300 Å in thickness. More preferably, the layer of a metal such as gold deposited on the surface of the support ranges from about 80 Å to about 250 Å in thickness or from about 90 Å to about 200 Å in thickness. Most preferably, the layer of the metal such as gold deposited on the support is from 100 Å or about 100 Å to 200 Å or about 200 Å. In some preferred embodiments, gold is deposited at an angle of from 30° or about 30° to 50° or about 50°. In other preferred embodiments, gold is deposited at an angle of 50° or about 50°. Different angles of metal deposition may be preferred depending on the particular application as will be apparent to those skilled in the art. The metallized surface obtained after deposition of the metal is generally an anisotropically rough and semi-transparent surface.

FIG. 1A is a schematic diagram showing the layer structure of a preferred device 10 for detecting the presence of a compound in a sample. The device 10 includes a substrate that includes a support 20 such as a glass slide and a metallized top surface 40 such as gold overlying a layer of an adhesion promoting material 30 such as titanium applied on top of support 20. A self-assembled monolayer 50 comprises an alkanethiol with a functional group that interacts with a moiety of a liquid crystal in a liquid crystal film 60 applied over self-assembled monolayer 50.

As noted above, the device for detecting the presence of a compound in a sample includes a surface with a functional group that reversibly or irreversibly interacts with (e.g. forms hydrogen bonds with, forms metal complexes with, has an acid-base interaction with, or covalently bonds) at least a portion of the compound to be detected. Although the use of a substrate with a metal surface as described above is not required, when such a surface is utilized it is highly preferred that the surface with a functional group that interacts with the compound is a SAM formed from a thiol such as, but not limited to, an alkanethiol with the functional group. Such thiols are typically adsorbed on the metallized surface of the support and may be used in conjunction with other thiols that do not contain the functional group that interacts with the compound. The alkanethiol may be adsorbed on the metallized surface from a solution that includes the thiol or thiols. In this manner, the alkanethiol will be adsorbed on the metallized surface forming a SAM that presents functional groups for interaction with the compound when it is present in a sample.

Various functional groups that interact with the compound to be detected may be used in accordance with the present invention. Examples of such groups include, but are not limited to: acids such as, but not limited to, carboxylic acids, hydroxamic acids, sulfonic acids, sulfinic acids, phosphonic acids, and phosphinic acids; metal complexes of acids such as metal carboxylates or metal sulfonates; nitrogen-containing functional groups such as pyridine, bipyridine, alkylamines, and phenylamines; metal complexes of amines; phosphines; metal complexes of phosphines; metal complexes of acetoacetoxy groups; ketones and aldehydes; and silicon-containing functional groups such as silanols. Preferred functional groups include carboxylic acids and metal carboxylates the latter of which are preferably formed by contacting a metal salt with a carboxylic acid. An especially preferred functional group is a carboxylic acid group on an alkanethiol and metal carboxylates formed therefrom. Preferred alkanethiols with carboxylic acid groups include alkanethiols with the formula $HS(CH_2)_nCO_2H$ where n is selected from 1, 2, 3, 4, 5, 6, 7, 8, 9, 10, 11, 12, 13, 14, 15, 16, 17, 18, 19, or 20 or more preferably where n is inclusively from 5 to 18, inclusively from 8 to 12, or where n is 10. Preferred metal carboxylates include those prepared from transition metals such as, but not limited to, Cu, Ag, Au, Zn, Ti, V, Cr, Mn, Fe, Co, Ni, Zr, Nb, Mo, Ru, Rh, Pd, Hf, Ta, W, Re, Os, Ir, and Pt, and other metals such as La, Sn, and Eu. In addition to the above list and $Cu^{+2}$, preferred metal salts for preparation of metal complex functional groups include $Ni^{2+}$, $I^{3+}$, $Zn^{2+}$, $Co^{2+}$, $Mn^{2+}$, $Fe^{3+}$, $V^{3+}$, $Sn^{4+}$, $La^{3+}$, $Ag^{1+}$, $Zr^{4+}$, and $Eu^{3+}$. Copper carboxylates, and particularly $Cu^{+2}$ carboxylates are particularly preferred metal carboxylate functional groups for use in the present invention although one skilled in the art will recognize that choice of the functional group and the moiety of the liquid crystal will depend on the type of compound to be detected.

Figure 15:
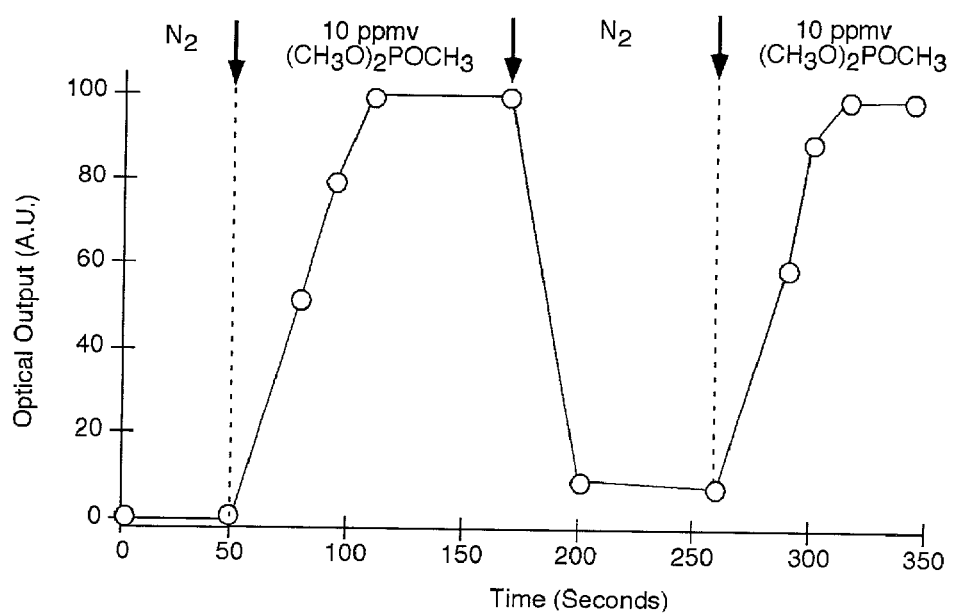
FIG. 15 is a graph showing the reversibility of dimethyl methylphosphonate (10 ppmv convected through a nozzle 3 mm from the surface of the film of 5CB) binding to 5CB coated SAM formed from HOOC($CH_2)_{10}$SH pretreated by immersion in a 100 mM solution of $Cu(ClO_4)_2$ as determined by luminance measurements.

The functional group of the surface may interact reversibly or irreversibly with the compound to be detected. If the interaction is reversible such as is the case when the compound is an organoamine, such as an alkylamine, and the functional group is carboxylic acid or when the compound is a dialkyl alkylphosphonate, such as dimethyl methylphosphonate, and the functional group is a $Cu^{+2}$ carboxylate, then the presence of the compound will result in a temporary change in the orientation of the liquid crystal as shown in FIG. 15. Such an arrangement is suitable for real-time detection of the compound in a sample such as a room or outdoor environment, and devices such as badges and sensors may be constructed that will rapidly indicate the presence of the compound to a wearer. If the interaction between the functional group and the compound is irreversible, then the device is suitable for measurement of chronic levels of exposure and a personal or area dosimeter may be manufactured.

As noted above, a preferred surface for detecting the presence of a compound in a sample includes a detection surface prepared by adsorbing an alkanethiol with a functional group for detecting the compound on a substrate having a top surface that contains the obliquely deposited gold or silver (the metallized surface) overlying a support. This is typically accomplished by immersing the substrate with the obliquely deposited gold or silver in a solution containing the alkanethiol. Alternatively, a solution may be dropped or poured onto the surface or otherwise contacted with the surface of the support containing the metal. The thiol (—SH) group of the alkanethiol binds to the metal on the support immobilizing the alkanethiol on the surface and forming a SAM. As noted above, the alkanethiol is often adsorbed onto the surface of the support from a solution containing the alkanethiol. In some embodiments, the alkanethiol is present in water or an alcohol such as ethanol or methanol although other liquids may also be employed in accordance with the invention.

Various alkanethiols without functional groups may be used in conjunction with the alkanethiol including the functional group to prepare suitable detection surfaces. Suitable such alkanethiols include, but are not limited to, $C_4$ to $C_{20}$ alkanethiols such as butanethiol, pentanethiol, hexanethiol, heptanethiol, octanethiol, nonanethiol, decanethiol, undecanethiol, dodecanethiol, tridecanethiol, tetradecanethiol, pentadecanethiol, hexadecanethiol, heptadecanethiol, octadecanethiol, nonadecanethiol, and eicosanethiol. More preferred alkanethiols include $C_5$ to $C_{16}$ alkanethiols, $C_6$ to $C_{16}$ alkanethiols, $C_8$ to $C_{14}$ alkanethiols, and $C_{10}$ to $C_{14}$ alkanethiols. Those skilled in the art will recognize that dialkyl disulfides, R—S—S—R, may also be used to prepare suitable detection surfaces. Generally, the amount of alkanethiol without the functional group will range from 0% to about 30%, from 0% to about 25%, or from 0% to about 20% of the total alkanethiols used. Preferred surfaces are prepared where the amount of alkanethiol without functional groups is 0% and the amount with functional groups is 100%, those where the amount of alkanethiol without functional groups is 10% and the amount with functional groups is 90%, and those where the amount of alkanethiol without functional groups is 20% and the amount of alkanethiol with functional group is 80% where the percentages are determined based on the total weight of alkanethiols used.

The concentration of the alkanethiol in the solution used for alkanethiol adsorption generally ranges from about 1 micromolar to 10 millimolar. A preferred concentration range is 100 micromolar to 2 millimolar, with adsorption times ranging from typically 2 minutes to 24 hours. A preferred adsorption time is between 1 hour and 6 hours. Typically, preferred surfaces were prepared by contacting metallized surfaces of a support with an ethanolic solution of an alkanethiol with a functional group such as $HOOC(CH_2)_{10}SH$ or a mixture of $HOOC(CH_2)_{10}SH$ and $H_3C(CH_2)_{10}SH$ at a total alkanethiol concentration of 1 mM for a period of at least about 1 hour. Longer or shorter contact times may be used as long as a densely packed monolayer is obtained as will be apparent to those of skill in the art. Generally, the lower the concentration of the alkanethiol in the alkanethiol solution, the longer the metallized surface will be contacted with the alkanethiol solution. Conversely, the higher the concentration of the alkanethiol in the alkanethiol solution, the shorter the metallized surface will be contacted with the alkanethiol.

The alkanethiols are typically adsorbed onto the metallized surface of the support in solutions at temperatures ranging from about 15° C. to about 50° C., from about 20° C. to about 40° C., from about 22° C. to about 40° C., or from about 25° C. to about 37° C. A preferred temperature range is from about 22° C. to about 28° C., and a more preferred temperature is about 25° C. or room temperature. A steady temperature is not necessary, and the temperature may be increased or decreased during the alkanethiol adsorption. Sometimes, improved thermal stability of a monolayer may be achieved by adsorbing the monolayer at an elevated temperature. Generally, the temperature of the alkanethiol solution is not critical to the preparation of the detection device. After an alkanethiol has been adsorbed onto the metallized surface of a preferred support, the surface of the support is typically rinsed with ethanol. The ethanol is then usually removed by blowing a stream of $N_2$ or other inert gas over the rinsed surface.

In one preferred device for detecting the presence of a compound in a sample, a support with a metallized top surface is first prepared and then a top surface is prepared using microcontact printing. In such a method, a stamp is first prepared using a polymer such as elastomeric polydimethylsiloxane. Such a stamp may be prepared by pouring a mixture of an elastomer such as Sylgard® 184CA brand polydimethylsiloxane (PDMS) in a master, such as a silicon master, with a curing agent in an appropriate curing ratio such as a 10:1 ratio of PDMS to curing agent. The width and depth of the relief may vary according to the application. In one application, the width of the relief was 15 µm and the depth of the relief was about 20 µm. After removal of entrained air bubbles such as by use of an applied vacuum, the mixture is allowed to cure. The stamp is then gently removed and rinsed. The rinsed stamp is then "inked" by placing a drop of a solution, such as ethanolic solution, containing alkanethiols on the stamp. In one procedure, the alkanethiols do not contain the functional group and include such alkanethiols as $H_3C(CH_2)_{11}SH$, $H_3C(CH_2)_{15}SH$, and combinations of such alkanethiols. The stamp is then typically dried and placed on a metallized surface such as an obliquely deposited gold surface for an appropriate period of time such as about 5 seconds. The stamped film of gold is then typically rinsed with a solvent such as ethanol or water and placed in a solution of an alkanethiol with a functional group or a mixture of an alkanethiol with a functional group and an alkanethiol(s) without such a group. For example, the stamped film may be placed in an ethanolic 1 mM solution of $HOOC(CH_2)_{10}SH$ and $H_3C(CH_2)_{11}SH$. This provides a surface with functional groups in areas defined by the stamping procedure. As one skilled in the art will readily recognize, the stamp may be treated with an alkanethiol containing a functional group that interacts with the compound and then placed in a solution of alkanethiols that do not include the functional group.

A surface presenting functional groups for interacting with a compound to be detected may also be prepared by contacting a metal salt with a first region of a metallized top surface that includes a functional group such as a carboxylic acid to prepare a first region with a metal carboxylate. Other regions of the metallized top surface may then be contacted with salts of other metals or with solutions of different concentrations to provide a device with different sensitivities towards compounds to be detected. For example, a metallized top surface that includes one region with $Cu^{+2}$ carboxylates and another region with carboxylic acids may be prepared such that amines are detected in one area and dialkyl alkylphosphonates are detected in the other regions. The spotting of the metal salts onto various parts of a surface may be done by hand using simple techniques, other techniques for spotting may be used that are known to those skilled in the art. For example, any spotting technology associated with the development of biological microarrays may be employed such as, but not limited to, gene chip spotting machines. This methodology may be extended to provide an array for the detection of multiple types of compound in a sample or to provide a device with differing sensitivities towards the compound.

Devices that contain surfaces with varying metal salts such as, but not limited to, metal carboxylates may be used beneficially to determine appropriate receptors for the detection of the compounds. For example a device with regions containing different metal salts of dimensions varying from micrometers to millimeters may be covered with a liquid crystal and then contacted with the compound to be detected. The response of each region may then be imaged for example as pixels and utilized in the selection of an appropriate metal salt for use in detecting the compound. The same methodology may be employed using a device where the same functional group is present, but different liquid crystals are used to determine the choice of an optimal liquid crystal.

Those skilled in the art will recognize that variations on the above procedure could also be used to produce a multiarray. In one such preferred procedure, rather than "spotting" droplets of liquid on a surface, a fluidic channel (e.g., made from micromolded polydimethylsiloxane) is used to deliver liquids to localized regions of a surface similar to the stamping method described above. Generally, any method known to those skilled in the art for delivering liquids to localized regions of a surface could be used to produce the preferred microarray devices for detecting compounds in samples.

The liquid crystals of the devices, optical cells, kits and methods of the present invention include a moiety that interacts with the functional group of the surface. If present in a sample, the compound or a portion of the compound displaces the liquid crystal from the functional group thereby altering the orientation of the liquid crystal on the surface with the functional group. Depending upon the compound to be detected and the liquid crystal and the functional group of the surface employed in the device, contact of the device with a sample containing the compound may either increase or decrease the uniformity of the orientation of the liquid crystal. As long as a detectable change in the orientation of the liquid crystal occurs upon contact with the sample, the device is suitable for detecting the presence of the compound. Therefore, the uniformity of the orientation of the liquid crystal may also remain about the same prior to and after contact with the compound to be detected so long as there is a change in the orientation that is detectable. For example, the orientation of the liquid crystal on a surface prior to contact may be planar and perpendicular after contact with the compound. The Examples demonstrate how the choice of functional group and liquid crystal may alter the orientation of the liquid crystal on a surface bearing the functional group. For example, prior to contact with an organoamine 5CB is oriented planar and parallel to the direction of gold deposition on a device comprising a glass support with an obliquely deposited gold surface and a SAM formed from an alkanethiol with a carboxylic acid functional group. On the other hand, 5CB is oriented perpendicular to the gold surface on a device comprising a glass support with an obliquely deposited gold surface and a SAM formed from an alkanethiol with a carboxylic acid functional group to which $Cu^{+2}$ has been complexed. Therefore, suitable liquid crystals of the present invention are those that include a moiety that reversibly interacts with the functional group that interacts with the compound.

Moieties that may be present on the liquid crystals include, but are not limited to, nitrile groups, carboxylic acid groups, pyridine, pyrimidine, fluoro, chloro, bromo, nitro and bipyridine groups. Liquid crystals with nitrile groups are more preferred for use in the present invention. Examples of liquid crystals with nitrile groups, include, but are not limited to, 4-cyano-4'-pentylbiphenyl (5CB), 7CB, and 8CB. A large listing of nitrile containing liquid crystals is presented in "Handbook of Liquid Crystal Research" by Peter J. Collings and Jay S. Patel, Oxford University Press, 1997, ISBN 0-19-508442-X. An especially preferred liquid crystal for use in the present invention is 4-cyano-4'-pentylbiphenyl. Although various types of liquid crystal may be employed, nematic liquid crystal are preferred. However, smectic liquid crystals formed from 8CB are also suitable for use in the present invention. The liquid crystal is preferably applied to the surface having the functional groups that interact with the compound before the device is exposed to the sample. However, it will be readily understood by those skilled in the art that the surface including the functional groups may be contacted with the sample followed by application of the liquid crystal. The liquid crystal may be applied to the surface using any technique known to those skilled in the art. In one embodiment for preparing an optical cell, a nematic liquid crystal is heated into its isotropic phase and drawn by capillary action into a space between two surfaces in an optical cell. In another embodiment, the liquid crystal is spin-coated onto the surface having a functional group such as a SAM. The thickness of the film of liquid crystal formed on top of the surface containing the functional groups preferably ranges from 1 µm to 100 µm, from 2 µm to 50 µm, from 5 µm to 20 µm, or more preferably is about 10 µm. The thickness of the liquid crystal on the surface with the functional groups is an important consideration as the compound to be detected must pass through the liquid crystal before it can interact with the functional groups in embodiments where the liquid crystal film is placed on the surface prior to contact with the sample.

A pumping device may be included in a device, optical cell, kit, or method of the invention. The pump will convect the sample to the surface of the liquid crystal increasing the sensitivity of the device and allowing detection of lower levels of the compound. Such a pump may be used in conjunction with a hollow tube to direct a flow of the sample to a specific area of the device.

Many types of compounds may be detected using the devices, optical cells, kits, and methods of the present invention. Examples of such compounds include, but are not limited to, organoamines and organophosphorus compounds, organosulfur compounds, organonitrogen compounds in addition to organoamines, cyanide compounds, nitrogen oxides, carbon monoxide, heavy metals, ketones, alcohols, and organic acids. Examples of organoamines that may be detected with the devices and methods of the present invention include alkylamines such as primary, secondary, and tertiary amines. One group of preferred alkylamines include those having the formula $H_2N(CH_2)_mCH_3$ where m is selected from 0, 1, 2, 3, 4, 5, 6, 7, 8, 9, or 10 or more preferably where m is 0 to 8, 0 to 6, or 6. Another group of preferred amines are biogenic amines such as, but not limited to, histamine, putrescine, and cadaverine. Where the compound to be detected is an amine, the functional group is preferably a carboxylic acid. Examples of phosphorus compounds that may be detected with the devices and methods of the present invention are organophosphonates such as, but not limited to dialkyl alkylphosphonates, such as, but not limited to, dimethyl methylphosphonate. Other organophosphorus compounds that may be detected include nerve agents and pesticides. The compound to be detected may be present in a gaseous or liquid sample or a gaseous sample that contains other vapors such as water, alcohols, hexanes, and/or ketones such as acetone.

The devices of the present application allow the presence of a compound in a sample to be ascertained. A method for detecting the presence of a compound in a sample includes contacting a device for detecting the presence of a compound in a sample with the sample. The device may include any of those described above and may include a second surface such that the device is an optical cell. Preferred devices include a substrate with a support that has a metallized top surface and a self-assembled monolayer. The self-assembled monolayer is preferably formed from an alkanethiol that is attached to the metallized top surface of the substrate and which includes a functional group that reversibly or irreversibly interacts with the compound as heretofore described. Preferred methods include disposing a liquid crystal with a moiety on the top surface of a self-assembled monolayer or other surface with the functional group. Finally, the method includes determining whether the orientation of the liquid crystal on the surface with the functional group, preferably the self-assembled monolayer, changes after the device contacts the sample. The absence of a change in orientation indicates the absence of the compound at detectable levels in the sample, whereas a visually detectable change in the orientation indicates that the compound is present in a sample.

The liquid crystal may be disposed on the top surface of the surface with the functional group before or after the device contacts the sample.

This is true because the interaction between the functional group and the compound, if present, will occur regardless of whether the liquid crystal is present on the surface. Preferably, however, the liquid crystal is disposed on the surface with the functional group prior to contact with the sample.

Preferred methods for detecting the presence of a compound in a sample include convecting the sample to the surface of the liquid crystal such as with a pump. This allows the detection of lower levels of the compound in a sample thus improving the sensitivity of the device.

The response of a liquid crystal device to the compound may be quantified using samples with known concentrations of the compound, and the distance that the compound penetrates into a film of the liquid crystal on the surface with the functional groups may be used to measure cumulative exposure to the compound. Furthermore, the instantaneous response of a liquid crystal device to the compound may be quantified by measuring the brightness of the light passing through the liquid crystal as explained in greater detail in the Examples that follow. Additionally, gradients in the concentration of a compound may be detected using the film of liquid crystal to image the distribution of concentration across a sample containing the compound.

Figure 1B:
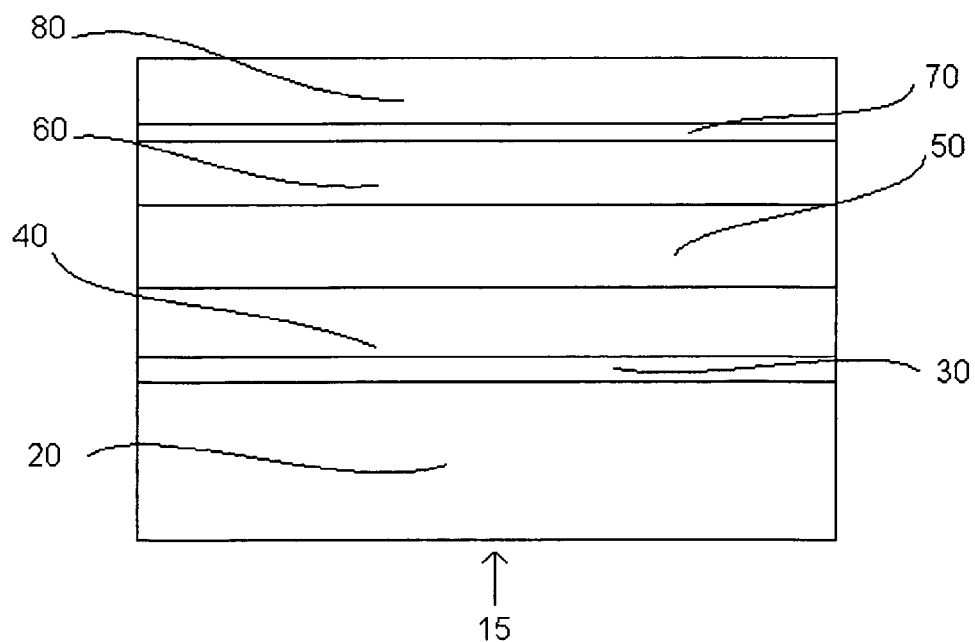

An optical cell for use in detecting the presence of a compound in a sample preferably includes a device for detecting the presence of a compound in a sample as described above. As shown in FIG. 1B, an optical cell may also include a spacing material, preferably a film 70, positioned parallel to but a spaced distance away from the top surface of the surface with the functional groups that interact with the compound. The spacing material and the top surface of the surface with a functional group for detecting the compound define a cavity that may be filled with a liquid crystal. Optical cells also preferably include a second surface 80 that uniformly aligns the liquid crystal when it contacts the surface. Such a second surface is preferably free of any functional group that interacts with the compound. The second surface of the optical cell contacts a first surface of the liquid crystal which is opposite a second surface of the liquid crystal that contacts the self-assembled monolayer of a preferred device for detecting the presence of a compound in a sample as described above. Typically, the spacing material, such as a film, is positioned between the detection surface and the surface that uniformly anchors liquid crystals. It is not required or necessarily preferred that both surfaces of the optical cell include functional groups that interact with the compound to be detected in a sample. For example, in some preferred optical cells, a second surface without functional groups is employed. An example of such a second surface is a SAM formed from an alkanethiol that does not have a functional group that interacts with the compound to be detected. The spacing material is preferably a film of a defined thickness that is preferably stable in the presence of the liquid crystal material, easy to handle, and does not contaminate the liquid crystal.

A variety of films are suitable for use as spacing materials in the optical cells according to the invention as will be apparent to those skilled in the art. A preferred film spacing material is preferably made of a polymeric material such as Mylar® brand film or Saran® brand wrap. The film spacing material is typically placed between the top of the surface with the functional groups and the surface that uniformly anchors liquid crystals such that the top of the surface with the functional groups and the surface that uniformly anchors liquid crystals face each other. The spacing material may also be comprised of microspheres or rods of defined diameter that are dispersed into the liquid crystal so as to separate the two surfaces forming the optical cell.

Kits for use in detecting the presence of a compound in a sample typically include a surface with functional groups that interact with the compound such as a substrate comprising a support with a metallized top surface with a SAM attached to it formed from an alkanethiol with a carboxylic acid or containing a metal carboxylate. Such kits may separately contain the substrate with the support and the metallized top surface and a thiol with a carboxylic acid functional group or may alternatively include a metallized top surface already containing a SAM formed from an alkanethiol containing a functional group. Kits also preferably include a liquid crystal with a moiety that interacts with the functional group of the alkanethiol as described above. Kits may further include a second surface that uniformly anchors liquid crystals and a spacing material such as a film adapted to be placed between the two surfaces to provide an optical cell as described above. The surface that uniformly anchors may include any of those described above. Preferred kits may include instructions for using the components to prepare a device that detects compounds and for how to detect compounds with the device. Preferred kits may also include one or more metal salts which may be solids or packaged as solutions. Such metal salts may be used to prepare the metal complex functional group of the devices of the invention.

EXAMPLES

The following materials and methodologies were utilized in the examples discussed in greater detail below.

Materials

Glass microscope slides used in the experiments marked premium grade were obtained from Fisher Scientific (Los Angeles, Calif.). Glass slides were cleaned prior to use by sequentially treating with "piranha solution" (70% $H_2SO_4$/ 30% $H_2O_2$) and base solution (70% KOH, 30% $H_2O_2$) using nitrogen to provide agitation (1 hour at 50° C.). "Piranha solution" should be handled with extreme caution because it reacts violently with organic materials and should not be stored in closed containers. The slides were then rinsed thoroughly in deionized water, ethanol and then methanol, and dried under a stream of nitrogen. Prior to use, the clean substrates were stored in an oven heated at 110° C. for at least 3 hours.

11-mercaptoundecanoic acid, $HOOC(CH_2)_{10}SH$, was prepared using previously published methods and can be purchased from Aldrich Chemical (Milwaukee, Wis.). E. B. Troughton, C. D. Bain, G. M. Whitesides, R. G. Nuzzo, D. L. Allara, M. D. Porter, *Langmuir*, 1988, 4, 365. The nematic liquid crystal, 4-cyano-4'-pentylbiphenyl (5CB) ($T_{ni}$=34.5° C.), manufactured by BDH, was purchased from EM Industries (Hawthorne, N.Y.). Dimethyl methylphosphonate (($H_3CO)_2P(=O)CH3$), $Cu(ClO_4)_2$ hexahydrate, and $Cd(NO_3)_2$ tetrahydrate were purchased from Alfa-Aesar (Ward Hill, Mass.). Hexanes, methanol, and from Fisher (Los Angeles, Calif.). Ethanol was purchased from Aaper (Shelbyville, Ky.). Titanium (99.999%) and gold (99.999%) were purchased from Advanced Materials (Spring Valley, N.Y.). Buffer solutions were prepared using analytical grade commercially available reagents.

Oblique Deposition of Gold

Semi-transparent films of gold with thicknesses of about 130 Å were deposited onto glass slides using an electron beam evaporator manufactured by Tek-Vac Industries (Brentwood, N.Y.). The gold was deposited from a fixed direction of incidence at an angle of incidence of 50° (measured from the normal of the surface). A 50 Å layer of titanium was used to promote adhesion between the glass and the film of gold. The rate of deposition of gold and titanium was about 0.2 Å/sec. The pressure in the evaporator was less than $1\times10^{-6}$ Torr before and during each deposition. The gold source was periodically cleaned by cycling between aqua regia (70% $HNO_3$, 30% HCl) and piranha solutions at 50° C. (30 minutes in each solution). The cycle was repeated 3 to 4 times, rinsing between cycles in deionized water.

Experiments Analyzing the Binding and Detection of Organoamines

Formation and Pretreatment of Self-Assembled Monolayers with Carboxylic Acid Functional Groups Self-assembled monolayers (SAMs) were formed on the surfaces of obliquely deposited films of gold by immersing the films in ethanolic solutions containing either 1 mM $HOOC(CH_2)_{10}SH$ or a mixture of $HOOC(CH_2)_{10}SH$ and $H_3C(CH_2)_{10}SH$ (1 mM total thiol concentration) for one hour. The composition of the mixed SAMs formed from $HOOC(CH_2)_{10}SH$ and $H_3C(CH_2)_{10}SH$ were estimated from contact angle measurements (see below). After rinsing in ethanol and drying under nitrogen, the SAMs were immersed for approximately one minute in aqueous solutions adjusted to pH 2.5 (about 1 mM HCl) or pH 3.2 (about 1 mM $H_3PO_4$). Upon removal from aqueous solution, the surface of a slide was placed under a stream of nitrogen gas to displace excess solution from the surface. Under these conditions, excess salts are not deposited onto the surface. All buffered solutions were used within 12 hours of preparation.

Formation of Patterned SAMs Using Microcontact Printing

An elastomeric stamp was prepared by pouring a mixture of Sylgard® 184CA brand polydimethylsiloxane (Dow Corning, Mich.) prepolymer and its curing agent in a 10:1 ratio onto a silicon master patterned with relief. The width of the relief was 15 µm and the depth approximately 20 µm. Entrained air bubbles were removed by applying a vacuum over the mixture of prepolymer and curing agent. The polymer mixture was allowed to cure for 12 hours at 50° C. The elastomeric stamp was then gently removed from the master and rinsed in ethanol. The stamps were "inked" by placing a drop of an ethanolic solution of 3 mM $H_3C(CH_2)_{11}SH$ or $H_3C(CH_2)_{15}SH$ onto the surface of the stamp. The stamp was then dried under a stream of nitrogen. The stamp was placed by hand into contact with the surface of a gold film and withdrawn after a period of about 5 seconds. The stamped film of gold was then rinsed in ethanol and placed into a 1 mM solution (see above) of $HOOC(CH_2)_{10}SH$ or mixtures of $HOOC(CH_2)_{10}SH$ and $H_3C(CH_2)_{10}SH$.

Gas Handling System for Dilution of Stock Gas Containing 20 or 7500 ppmv of n-Hexylamine The concentration of n-hexylamine in a nitrogen stream was controlled to about 500 parts-per-trillion by volume (pptv) using a home-built gas handling system. Combinations of mass flow controllers (5850E Brooks Instruments, Pa.) with flow ranges (at STD) up to 10, 500, and 5000 $cm^3$/min were used to mix gas streams to desired concentrations and to deliver these streams at specified flow rates. All components, Swagelock® brand fittings, check valves (⅓ psig), ⅛" tubing were constructed from stainless steel wrapped in heat tape (rated to temperatures >150° C.). The system was heated after each experiment in order to desorb any n-hexylamine that could have adsorbed to the walls of the flow system.

Binding of n-Hexylamine to SAMs Formed from $HOOC(CH_2)_{10}SH$

SAMs formed from $HOOC(CH_2)_{10}SH$ were exposed to $H_2N(CH_2)_5CH_3$ (between 500 pptv to 7500 ppmv in nitrogen) for two minutes using the dilution system described above for n-hexylamine. Samples were exposed in a circular flow cell (volume=50 $cm^3$) at a flowrate of 500 $cm^3$/min or by flow through a nozzle with an inner diameter of ¹⁄₃₂" that was placed at a set distance from the surface. The position and distance of the nozzle from the surface was set by attaching this nozzle to a home-built XYZ translation stage. After exposure, the SAM was immediately removed from the system and subsequently contacted with a liquid crystal (see below). By ellipsometry (see below), it was determined that n-hexylamine remained bound to the SAM for at least 5 minutes after removal from the flow cell. However, n-hexylamine had largely desorbed from the SAM under ambient conditions after about 60 minutes indicating the reversible binding of the organoamine to the functional groups of the alkanethiol of the SAM.

Ellipsometry for Studies of Organoamines

Ellipsometric thicknesses of SAMs were measured after immersion in aqueous solution (pH 3.2) and before and after exposure to n-hexylamine using a Rudolph Auto EL ellipsometer (Flanders, N.J.) at a wavelength of 6320 Å and an angle of incidence of 70°. Measurements were performed using films of gold with thicknesses of 2000 Å that were deposited without a preferred direction or angle of incidence. Ellipsometric constants were measured immediately following removal of the gold films from the evaporator. The ellipsometric thicknesses of SAMs were estimated using a three layer model assuming a refractive index of 1.46 for the monolayer. Because the optical constants of gold are known to vary slightly between batches, prior to performing the experiments, determinations were made of the ellipsometric thicknesses of SAMs formed from $H_3C(CH_2)_{15}SH$ (23±1 Å), $H_3C(CH_2)_7SH$ (12±1 Å), and $HOOC(CH_2)_{10}SH$ (17±1) Å on each gold substrate (1 cm×2.5 cm). In order to minimize drift in the measurements, the ellipsometer was re-initialized every hour during the experiments.

Contact Angle Determinations

Advancing and receding contact angles were measured using a Ramé-Hart Model 100 (Mountain Lakes, N.J.) goniometer at room temperature. Measurements of contact angles under cyclooctane were performed inside a glass cell that was cleaned with piranha solution prior to use. Advancing and receding contact angles were measured using an aqueous solution at pH 2.5 or pH 3.2. For a description of contact angle measurement methodology see P. Pieranski, B. Jérôme, Phys. Rev. A. 1989, 40, 314; J. Bechhoefer, B. Jérôme, Phys. Rev. A. 1989, 48, 4556.

Orientations of Liquid Crystals

The orientations of nematic phases of 5CB on SAMs were determined using optical cells fabricated from two films of gold, each of which supported SAMs. The gold films were aligned (facing each other) such that the direction of deposition of the gold in each film was parallel. The gold films were spaced apart with a thin film of Mylar or Saran Wrap (nominal thickness 2 or 12 μm). A drop of 5CB, heated into its isotropic phase (T<45° C.), was then drawn by capillary action into the cavity between the two surfaces of the optical cell. The cell was subsequently cooled to room temperature, and the optical texture was analyzed with an Olympus BX-60 polarizing light microscope (Tokyo, Japan) in transmission mode. The optical textures were observed to be invariant for at least 1 to 2 hours following contact of the liquid crystal with the SAMs.

Measurement of Out-of-Plane Orientations of Liquid Crystals

A home-built optical apparatus was used to measure the out-of-plane orientation (tilt) of 5CB within the optical cells. The optical cells were placed between cross-polars, illuminated at normal incidence using a polarized He—Ne laser, and then rotated from −20° to +20° with respect to the normal. A plot of the intensity of light transmitted through the cell against the angle of incidence was used to estimate the tilt of the optical axis of the liquid crystal from the surface of the cell.

Measurement of In-Plane Orientations of Liquid Crystals

Optical cells were assembled from two SAMs pretreated by immersion and withdrawal from aqueous solutions at pH 3.2 and then exposed to 7,500 ppmv n-hexylamine (for two minutes). The azimuthal orientations of liquid crystals supported on SAMs was measured using white light, crossed polarizers, a quarter wave plate (QWP), and about 2 μm-thick optical cells. The orientation of the optical axis of the liquid crystal (the director) was determined by rotating the cell between cross polarizers and observing the shift in interference colors upon insertion of the QWP into the optical path. The in-plane orientation of the liquid crystal was defined as the one for which the insertion of the QWP resulted in the maximum positive shift in interference colors. The interference colors were interpreted by using a Michel-Levy color chart.

Experiments Analyzing the Binding and Detection of Organophosphorus Compounds

Formation and Pretreatment of Self-Assembled Monolayers with Metal Carboxylate Functional Groups Self-assembled monolayers (SAMs) were formed on the surfaces of obliquely deposited films of gold by immersing the films in ethanolic solutions containing 1 mM HOOC $(CH_2)_{10}SH$ for one hour. After rinsing in ethanol and drying under nitrogen, the SAMs were immersed for 5 minutes in ethanolic solutions of $Cu(ClO_4)_2$ or $Cd(NO_3)_2$. The areal density of the metal was manipulated by controlling the concentration of copper or cadmium in solution between 0.1 µM to 100 mM. Upon removal from the ethanol, the surface of a slide was rinsed with ethanol and then placed under a stream of nitrogen gas to displace excess solution from the surface. All copper and cadmium solutions were used within 6 hours of preparation.

Gas Handling System for Dilution of Dimethyl Methylphosphonate

The vapor pressure of $(H_3CO)_2P(=O)CH_3$ is about 900 ppmv at 25° C. By flowing nitrogen through a gas-sparger filled with $(H_3CO)_2P(=O)CH_3$ in the liquid state, the vapor concentration of $(H_3CO)_2P(=O)CH_3$ could be controlled down to about 20 parts-per-billion by volume (ppbv) using a home-built gas handling system. Combinations of mass flow controllers (5850E Brooks Instruments, PA) with flow ranges (at STD) up to 10, 500, and 5000 $cm^3$/min were used to dilute gas streams to desired concentrations and deliver these streams at specified flow rates. All components, Swagelock® brand fittings, check valves (⅓ psig), and ⅛" tubing were constructed from stainless steel wrapped in heat tape (rated to temperatures >150° C.). The system was heated after each experiment in order to desorb any $(H_3CO)_2P(=O)CH_3$ that could have adsorbed onto the walls of the flow system.

Ellipsometry for Studies of Organophosphonates the ellipsometric thicknesses of SAMs and spin-coated films of 5CB were measured using a Rudolph Auto EL ellipsometer (Flanders, N.J.) at a wavelength of 6320 Å and an angle of incidence of 70°. Measurements were performed using films of gold with thicknesses of 1000 Å that were deposited without a preferred direction or angle of incidence. Ellipsometric constants were measured immediately following removal of the gold films from the evaporator. The ellipsometric thicknesses of SAMs were estimated using a three layer model assuming a refractive index of 1.46 for the monolayer. Drift in the measurements was minimized by re-initializing the ellipsometer every hour during the experiments. The ellipsometric thickness of SAMs formed from $H_3C(CH_2)_{15}SH$ (23±1 Å), $H_3C(CH_2)_7SH$ (12±1 Å), and $HOOC(CH_2)_{10}SH$ (17±1 Å) on each gold substrate was again verified because the optical constants of gold are known to vary slightly between different microscope slides evaporated in the same batch.

X-ray Photoelectron Spectroscopy of SAMs with Metal Carboxylates

X-ray photoelectron spectroscopy (XPS) (Perkin-Elmer Phix 5400) was used to measure the amount of copper or cadmium complexed to SAMs formed from $HOOC(CH_2)_{10}$ SH and the metal salts as described above. XPS was also used to look for the presence of excess salts and contaminants on the surfaces of the SAMs following their immersion in ethanolic solutions of $Cu(ClO_4)_2$ or $Cd(NO_3)_2$. The chamber pressure during acquisition of all XPS spectra was 0.5 to $3\times10^{-8}$ Torr and the spot size was 250 µm×1000 µm. The intensity of X-rays emitted from the Al-Kα anode varied by about 2% over a 12 hour period. Survey scans with a pass energy of 89.45 eV were acquired at each location on the sample. Element specific acquisitions (in multiplex mode) were performed with a pass energy of 35.75 eV centered on the O (1s), C (1s), N(1s), Cl(2p), Au($4f_{5/2}$, $4f_{7/2}$), Cu($2p_{1/2}$, $2p_{3/2}$), and Cd(3p,3d) peaks and each element was corrected for its specific Scofield cross section. The area of the Au ($4f_{5/2}$, $4f_{7/2}$) peaks varied by less than 10% from sample to sample. The binding energies were referenced to the Au($4f_{7/2}$) peak at 84 eV.

Even though the valence state of the Cu or Cd in the ethanolic solution used to form the metal carboxylates was known, the stoichiometry of the metal and the carboxylate group complex at the surface could not be determined because the amount of ethanol incorporated into the surface was unknown. However, the areal density of metal complexed to the SAM was obtained by determining the ratios of the areas of the metal peaks (Cu $2p_{1/2}$ or Cd $3d_{3/2}$) after formation of the metal-carboxylic acid complex and the O(1s) peaks (prior to formation of the complex).

Films of Liquid Crystals Formed by Spin Coating

Thin films of liquid crystals (about 4 µm) on SAMs formed from $HOOC(CH_2)_{10}SH$ complexed with copper were prepared by spin coating about 10 µl of 5CB (in the nematic phase) using a photoresist spinner (Headway Research, Inc., Texas). 5CB was injected onto the surface rotating at 5000 rpm at room temperature. The sample was rotated for 20 seconds. The thickness of spin-coated films of nematic 5CB was measured by placing the spin-coated substrate on a heated stage maintained at 40° C. (Reichert-Jung, Austria). At this temperature, the film of 5CB was in the isotropic state and the refractive index of the film was assumed to be 1.589. The resultant thickness of the liquid crystal film (heated into the isotropic state) as measured by ellipsometry was 3.5+/−0.7 µm.

Orientations of Liquid Crystals

The orientations of nematic phases of 5CB and n-(p-methoxy-benzylidene)-p-n-butylamine (MBBA) on SAMs was measured using optical cells fabricated from two films of gold, each of which supported SAMs and using thin films of liquid crystals deposited onto surfaces by spin coating as described above. The optical cells were fabricated using two gold films that were aligned (facing each other) such that the direction of deposition of the gold in each film was parallel. The gold films were spaced apart with a thin film of Mylar or Saran Wrap (nominal thickness 2 µm). A drop of 5CB, heated into its isotropic phase (T<45° C.), was drawn by capillary action into the cavity between the two surfaces of the optical cell. The cell was subsequently cooled to room temperature, and the optical texture was analyzed with an Olympus BX-60 polarizing light microscope (Tokyo, Japan) in transmission mode.

Measurement of In-Plane Orientations of Liquid Crystals

The azimuthal (in-plane) orientations of liquid crystals supported on SAMs was measured using white light, crossed polarizers, a quarter wave plate (QWP), and either about 2 µm to 4 µm-thick optical cells or thin films of 5CB. Within the films of 5CB, the orientation of the liquid crystal was not uniform across the thickness of the film because (with 5CB, for example) homeotropic anchoring occurs at the air-5CB interface while planar anchoring can be induced at the SAM-5CB interface. Nevertheless, the azimuthal orientation of the optical axis of the liquid crystal (the director) within the optical cell or the film could be determined by rotating the cell between cross polarizers and observing the shift in interference colors upon insertion of the QWP into the optical path. The in-plane orientation of the liquid crystal was defined as the one for which the insertion of the QWP resulted in the maximum positive shift in interference colors. The interference colors were interpreted by using a Michel-Levy color chart.

Binding of Dimethyl Methylphosphonate to SAMs Formed from Copper Carboxylates A thin film of 5CB (approximately 4 µm) supported on a SAM formed from $HOOC(CH_2)_{10}SH$ immersed in an ethanolic solution of 100 mM $Cu(ClO_4)_2$ as described above was exposed to vapor phase $(CH_3O)_2P(=O)CH_3$ at a concentration of between 20 ppbv to 900 ppmv in nitrogen using the dilution system described above. These samples were exposed either in a circular flow cell (volume=50 cm$^3$) at a flowrate of 500 cm$^3$/min or by flow through a stainless steel (or glass) nozzle with an inner diameter of $\frac{1}{32}$" that was placed at set a distance from the surface. The position and distance of the nozzle from the surface was set by attaching this nozzle to a home-built XYZ translation stage.

Image Capture and Analysis

Images of the optical appearance of the liquid crystal (between cross polars) were captured with a digital camera (C-2020Z, Olympus, Melville, N.Y.) that was attached to a polarized light microscope (BX60, Olympus, Melville, N.Y.). A quantitative comparison of the textures was made using computer software (NIH Image, Bethesda, Md.) to calculate the average luminance (average pixel value on a scale of 0 to 255) of the image after conversion of the image from color to gray scale. Consistent settings of the microscope light source (50% of maximum intensity and 25% open aperture) and digital camera (11m f-stop $\frac{1}{100}$ shutter speed) were used to permit the comparison of values of luminance between samples. The raw luminance of each sample (S) was corrected for the luminance of an image of the liquid crystal supported on the mixed SAM (no bound $(CH_3O)_2P(=O)CH_3$; $S_{min}$) and normalized by the corrected, maximum luminance of the images of liquid crystals supported on SAMs on which a full coverage of $(CH_3O)_2P(=O)CH_3$ was bound ($S_{max}$ at t=about 1 minute for 2 mm spacing and t=about 3 minutes for 3 mm spacing). Variations in $S_{min}$ and $S_{max}$ were found to be small (about 5%) from batch to batch of samples. The equation used to calculate the normalized and corrected luminance (optical output), L is given by the formula:

$$L(\%) = \left(\frac{S - S_{min}}{S_{max} - S_{min}}\right) \cdot 100$$

Discussion of Experimental Results

Experimental Results Related to Organoamine Detection

Orientations of Nematic 5CB on n-Hexylamine Bound to SAMs with Carboxylic Acid Groups The out-of-plane orientations of 5CB supported on SAMs including the carboxylic acid functional group to which $N_2N(CH_2)_5CH_3$ was bound were analyzed. The thickness of the layer of liquid crystal within the cavity of the optical cell was about 12 µm and the direction of deposition of gold supporting each SAM was parallel within the cell. By mounting these cells in the crystal rotation apparatus, the tilt of the optical axis of 5CB from the plane containing the SAM was determined to be less than 1° for cells with SAMs presenting either COOH or COOH groups to which $H_2N(CH_2)_5CH_3$ was bound. That is, the orientation of 5CB on these surfaces was planar. No measurable change in the tilt of the liquid crystals was evident upon binding of $H_2N(CH_2)_5CH_3$.

The in-plane (azimuthal) orientation of 5CB on SAMs formed from $HOOC(CH_2)_{10}SH$ to which $H_2N(CH_2)_5CH_3$ was bound was also measured. The thickness of the cavity within the optical cell was about 2 to 4 µm, and the direction of deposition of gold supporting each SAM was parallel within the cell. The optical textures (and thus the orientation of 5CB) were observed to be uniform across all optical cells and no bulk distortion (twist, bend, or splay) of the liquid crystal within the cells was observed. The azimuthal orientation of the liquid crystal was determined by noting the change in interference colors upon insertion of a quarter-wave plate into the optical path. When using cells formed with SAMs formed from $HOOC(CH_2)_{10}SH$ pretreated at pH 3.2, 5CB was observed to orient parallel to the direction of deposition of the gold. In contrast, when using SAMs formed from $HOOC(CH_2)_{10}SH$ to which $H_2N(CH_2)_5CH_3$ was bound, 5CB oriented perpendicular to the direction of deposition of the gold.

Enhancement of Optical Contrast by Removal of Twist-Distortion within Nematic 5CB upon Binding of n-Hexylamine Whereas the results described above establish that $H_2N(CH_2)_5CH_3$ bound to a SAM formed from $HOOC(CH_2)_{10}SH$ drives an in-plane, 90° change in the azimuthal orientation of 5CB, these results were based on the interpretation of interference colors and the use of a quarter wave plate, both of which are inconvenient. Therefore, an optical cell was designed that provides a level of optical contrast that is sufficiently high so as to provide obvious reporting of the presence of a bound organoamine such as n-hexylamine to a SAM containing an alkanethiol with a functional group such as a carboxylic acid such as $HOOC(CH_2)_{10}SH$. The fabrication of these optical cells used asymmetric surfaces such that the binding of $H_2N(CH_2)_5 CH_3$ to the carboxylic acid groups on the alkanethiol of the SAM resulted in the removal of a twist distortion within a nematic liquid crystal.

The optical textures of 5CB confined within cells fabricated using a SAM formed from $H_xC(CH_2)_{14}SH$ on one surface and a SAM formed from $HOOC(CH_2)_{10}SH$ on the opposing surface were observed. Prior to contact with a sample containing $H_2N(CH_2)_5CH_3$, the optical cell appeared bright when viewed between crossed polars. In contrast, the optical cell appeared dark between parallel polars. These optical characteristics indicated that 5CB was oriented with a twist distortion within the optical cell. When the SAM formed from $HOOC(CH_2)_{10}SH$ was exposed to 12 ppmv $H_2N(CH_2)_5CH_3$ for 2 minutes, however, the cell appeared dark between crossed polars. These optical characteristics indicate uniform alignment within the liquid crystal phase after exposure to the amine. The removal of the twist distortion within the liquid crystal indicates that the SAM supporting bound $H_2N(CH_2)_5CH_3$ imposed an azimuthal orientation on a liquid crystal that is parallel to the orientation imposed by $H_3C(CH_2)_{14}SH$.

In the above experiments, the binding of $H_2N(CH_2)_5CH_3$ to SAMs formed from $HOOC(CH_2)_{15}SH$ was transduced by removal of the twisted nematic structure of 5CB. The binding of $H_2N(CH_2)_5CH_3$ induced 5CB to orient in an azimuthal direction that is perpendicular to the direction of gold deposition. This behavior results from a very weak azimuthal anchoring energy on the SAMs bound with $H_2N(CH_2)_5CH_3$. For example, when the opposing surface (such as a SAM formed from $H_3C(CH_2)_{15}SH$ or $HOOC(CH_2)_{10}SH$ was used), the orientation of 5CB was found to be parallel to the direction of gold deposition. That is, optical cells constructed from $H_3C(CH_2)_{15}SH$ on one surface and $H_2N(CH_2)_5CH_3$ bound to SAMs formed from $HOOC-(CH_2)_{10}SH$ on the opposing surface do not support a twist distortion. Rather, a uniform orientation of 5CB parallel to the direction of gold deposition was obtained. When the above observations are combined, they lead to the conclusion that the in-plane anchoring energy of surfaces formed by the binding of $H_2N(CH_2)_5CH_3$ to the carboxylic acid functional group are weaker than the azimuthal anchoring energy on SAMs formed from $H_3C(CH_2)_{15}SH$ or $HOOC(CH_2)_{10}SH$.

Figure 2A:
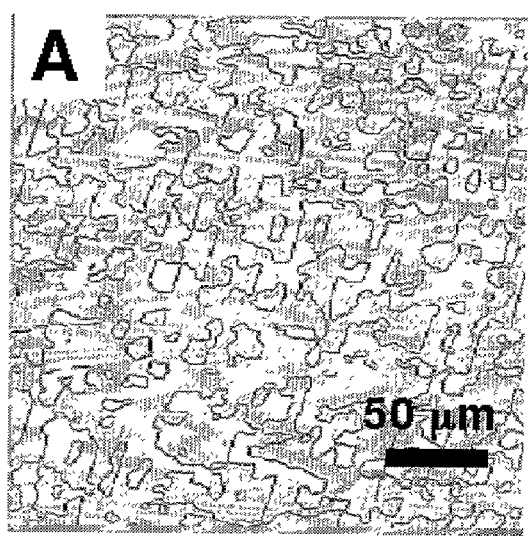
FIGS. 2A and 2B are drawings showing the optical textures (cross polars) formed by nematic 5CB within optical cells (thickness of about 12 μm) prepared with one surface supporting a SAM patterned using $H_3C(CH_2)_{14}SH$ and an opposing surface supporting a SAM patterned using $HOOC(CH_2)_{10}SH$ and $H_3C(CH_2)_{11}SH$ pretreated at a pH of 3.2 prior to exposure to n-hexylamine (FIG. 2A) and after exposure (FIG. 2B) to a gaseous sample containing 12 ppmv of n-hexylamine for 2 minutes.
Figure 2B:
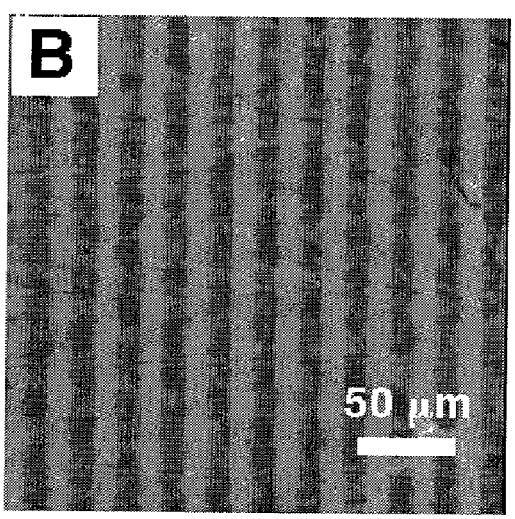

As illustrated in FIGS. 2A and 2B, another technique that may be employed to enhance the optical contrast upon binding of a compound in a sample is spatial, localized binding of a compound such that a diffraction grating is formed. FIG. 2A shows the optical texture of 5CB (cross polars) within a cell fabricated (as above) using a SAM formed from $H_3C(CH_2)_{14}SH$ on one surface and on the other surface a SAM patterned from $H_3C(CH_2)_{11}SH$ and $HOOC(CH_2)_{10}SH$ formed using microcontact printing. Prior to contact with a sample comprising an organoamine compound, these surfaces produced a twist distortion within the 5CB throughout the cell. The +/−½ line defects separate areas that have a reversal in the direction of twist. Upon exposure to a sample containing $H_2N(CH_2)_5CH_3$, however, the regions presenting COOH bind the $H_2N(CH_2)_5CH_3$ and cause, locally, the 5CB to adopt the same orientation as the upper surface (SAM formed from $H_3C(CH_2)_{14}SH$). In contrast, the 5CB anchored between the SAMs formed from $H_3C(CH_2)_{11}SH$ and $H_3C(CH_2)_{14}SH$ remained twisted after exposure of the patterned SAM to $H_2N(CH_2)_5CH_3$, thus resulting in the formation of the diffraction grating as shown in FIG. 2B (cross polars). This methodology and optical cell device allows a simple determination of whether or not a compound is present in a sample.

Figure 3:
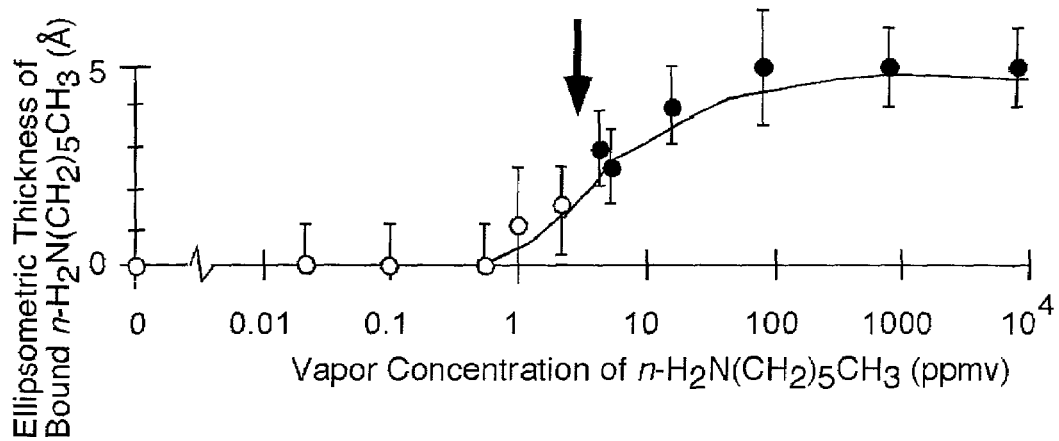
FIG. 3 is a graph showing the ellipsometric thickness of bound n-hexylamine as a function of the vapor concentration of n-hexylamine in ppmv for a SAM formed from $HOOC(CH_2)SH$ where ● indicates an in-plane orientation of 5CB that is perpendicular to the direction of gold deposition and ○ indicates an in-plane orientation of 5CB that is parallel to the direction of gold deposition.

Sensitivity of Nematic 5CB to Binding of Organoamines to SAMs Containing Carboxylic Acid Functional Groups The above results demonstrate the design of two types of optical cells in which the binding of an organoamine such as, but not limited to, $H_2N(CH_2)_5CH_3$, to a functional group, such as, but not limited to, a carboxylic acid, on an alkanethiol of a SAM formed from an alkanethiol, such as $HOOC(CH_2)_{10}SH$, may be used in conjunction with a liquid crystal to detect the presence of an organoamine in a sample. In order to determine how the orientation of the 5CB changed as a function of the amount of $H_2N(CH_2)_5CH_3$ bound to the SAM, measurements of the ellipsometric thickness of bound $H_2N(CH_2)_5CH_3$ and the orientations of 5CB supported on SAMs formed from $HOOC(CH_2)_{10}SH$ to which different amounts of $H_2N(CH_2)_5CH_3$ was bound were conducted. The amount of bound $H_2N(CH_2)_5CH_3$ was varied by manipulating the concentration of $H_2N(CH_2)_5CH_3$ in a nitrogen stream between 0.01 ppmv and about 7,500 ppmv at a flow rate of 500 cm$^3$/min. The surface was contacted with the nitrogen stream for 2 minutes in these experiments. FIG. 3 shows that bound $H_2N(CH_2)_5CH_3$ with an ellipsometric thickness of ±2 Å is sufficient to cause 5CB to adopt an orientation that is orthogonal to that observed in the absence of the organoamine in a sample. Under these conditions, a measurable change in the in-plane orientation of 5CB occurred at a bulk vapor concentration of $H_2N(CH_2)_5CH_3$ between 2 ppmv to 3 ppmv as indicated by the arrow in the figure. The transition in the in-plane orientation of 5CB was discontinuous as indicated by the bold arrow shown in FIGS. 3 and 4. The orientation of 5CB was observed to be uniform across each SAM unless the SAM was deliberately patterned such as described above where a diffraction grating was formed.

The Use of Mixed SAMs for Increasing Detection Sensitivity

The above results demonstrate that the azimuthal orientations of 5CB on SAMs formed from alkanethiols with functional groups such as carboxylic acids ($HOOC(CH_2)_{10}SH$) change discontinuously as a function of the amount of $H_2N(CH_2)_5CH_3$ in a sample. Because the transition was discontinuous at a specific coverage, further investigations were made to determine whether changes in the orientation of 5CB at designed coverages of $H_2N(CH_2)_5CH_3$ could be accomplished (including coverages lower than that found to trigger the change in orientation of 5CB on SAMs formed from $HOOC(CH_2)_{10}SH$). The approach used was based on the preparation of mixed SAMs formed from $HOOC(CH_2)_{10}SH$ and $H_3C(CH_2)_{10}SH$. Mixed SAMs were formed using $H_3C(CH_2)_{10}SH$ because $H_3C(CH_2)_{10}SH$ orients 5CB in a direction perpendicular to the direction of deposition of the gold. By forming mixed SAMs from $H_3C(CH_2)_{10}SH$ and $HOOC(CH_2)_{10}SH$, it was hypothesized that the amount of $H_2N(CH_2)_5CH_3$ in a sample that is needed to trigger a change in the azimuthal orientation of 5CB could be lowered. The maximum amount of $H_3C(CH_2)_{10}SH$ that could be introduced into the mixed SAM while maintaining an alignment of 5CB parallel to the direction of gold deposition was determined to be about 20% $H_3C(CH_2)_{10}SH$. This mixed SAM was prepared by immersing a gold film into an ethanolic solution containing 0.91 mM $HOOC(CH_2)_{10}SH$ and 0.09 mM $H_3C(CH_2)_{10}SH$ for 60 minutes.

Figure 4:
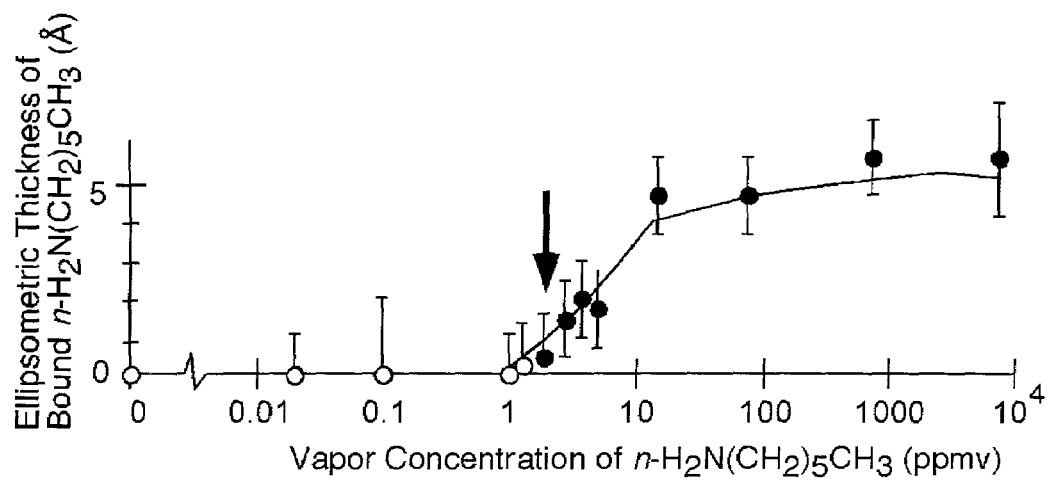
FIG. 4 is a graph showing the ellipsometric thickness of bound n-hexylamine as a function of the vapor concentration of n-hexylamine in ppmv for a SAM formed from 80% $HOOC(CH_2)SH$ and 20% $H_3C(CH_2)_{10}SH$ where ● indicates an in-plane orientation of 5CB that is perpendicular to the direction of gold deposition and ○ indicates an in-plane orientation of 5CB that is parallel to the direction of gold deposition.

As shown in FIG. 4, when mixed SAMs were utilized, the change in orientation of 5CB was observed to be triggered by exposure of the SAM to 1.5 ppmv to 2 ppmv $H_2N(CH_2)_5$ $CH_3$ for 2 minutes. The associated change in ellipsometric thickness caused by binding of $H_2N(CH_2)_5CH_3$ was not measurable (<1 Å). These results show that the amount of bound n-hexylamine that triggers the change in the orientation of 5CB is below the limits of detection of the ellipsometric methods employed. The n-hexylamine thus triggered a change in the orientation of the 5CB on the mixed SAM at a lower vapor concentration and a lower ellipsometric thickness of bound material as compared to experiments based on SAMs formed from $HOOC(CH_2)_{10}$ SH (see above). Use of the mixed SAM increased the sensitivity of 5CB to the vapor concentration of $H_2N(CH_2)_5$ $CH_3$ by a factor of about 2 as compared to SAMs formed solely from $HOOC(CH_2)_{10}SH$.

Figure 5:
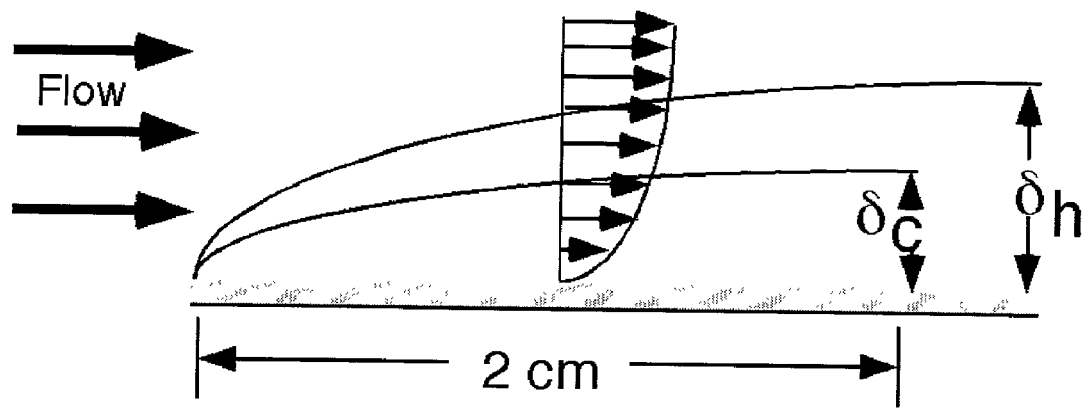
FIG. 5 is a schematic illustration of the concentration and hydrodynamic boundary layers for a liquid crystal on a SAM.

Sensitivity of 5CB to Vapor Phase Concentrations of n-Hexylamines-Role of Mass Transport Order of magnitude estimates of transport of $H_2N(CH_2)_5$ $CH_3$ to the SAMs suggest that the amount of bound $H_2N$ $(CH_2)_5CH_3$ is limited by diffusion (FIG. 5). The thickness of the concentration boundary layer, $\delta_c$, can be estimated as $\delta_c$ about $(D_{ab}x/V_{max})0.5$ where $D_{ab}$ is the diffusivity (0.05 $cm_2$/sec for $H_2N(CH_2)_5CH_3$), x is the length of the developing boundary layer (2 cm), and $V_{max}$ is the velocity of the gas. For gas velocities of 1 cm/sec, a boundary layer with a thickness of about 0.5 cm was calculated. In order to estimate how this boundary layer thickness affected the transport of $H_2N(CH_2)_5CH_3$ to the SAM, the surface coverage of bound $H_2N(CH_2)_5CH_3$ was calculated, as $\theta$ (mol/m$^2$), by $\theta=C_aD_{ab}t/\delta_c$, where t is the time of exposure (2 minutes) and $C_a$ ranges from 0.01 ppmv to 10 ppmv. By assuming the surface area occupied by each COOH group to be 20 Å, a 20% coverage at 4 ppmv (where a transition in the orientation of 5CB was observed) and a 2% coverage at 400 ppbv (where a transition in orientation of 5CB was not observed) was calculated. A coverage of 20% corresponds to a measured ellipsometric thickness of 2 Å. In the case of 400 ppbv, a coverage of 2% corresponds to a change in ellipsometric thickness of 0.2 Å. These results indicate 400 ppb leads to bound $H_2N(CH_2)_5CH_3$ with a thickness less than 1 Å. In short, these mass transport calculations predict surface coverages similar to values that we measured experimentally. Thus, it was concluded that the amount of $H_2N(CH_2)_5$ $CH_3$ bound to the surface in the previously described experiments was limited by diffusion.

Figure 6:
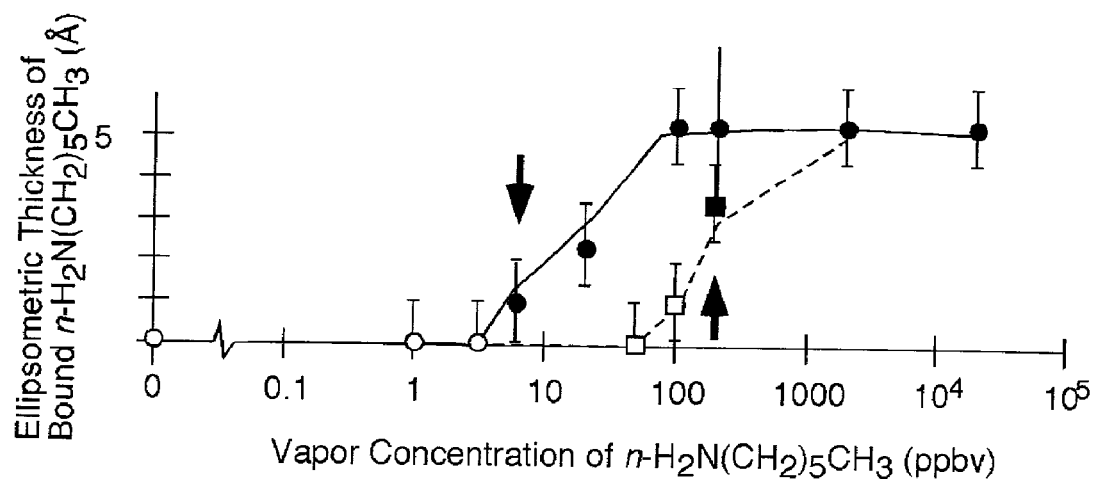
FIG. 6 is a graph showing the ellipsometric thickness of bound n-hexylamine as a function of the vapor concentration of n-hexylamine in ppbv for a SAM formed from HOOC($CH_2$)SH with a nozzle spaced 1 mm (● and ○) and 2 mm from the SAM (■ and □) where ● and ■ indicate an in-plane orientation of 5CB that is perpendicular to the direction of gold deposition and □ and ○ indicate an in-plane orientation of 5CB that is parallel to the direction of gold deposition.
Figure 7:
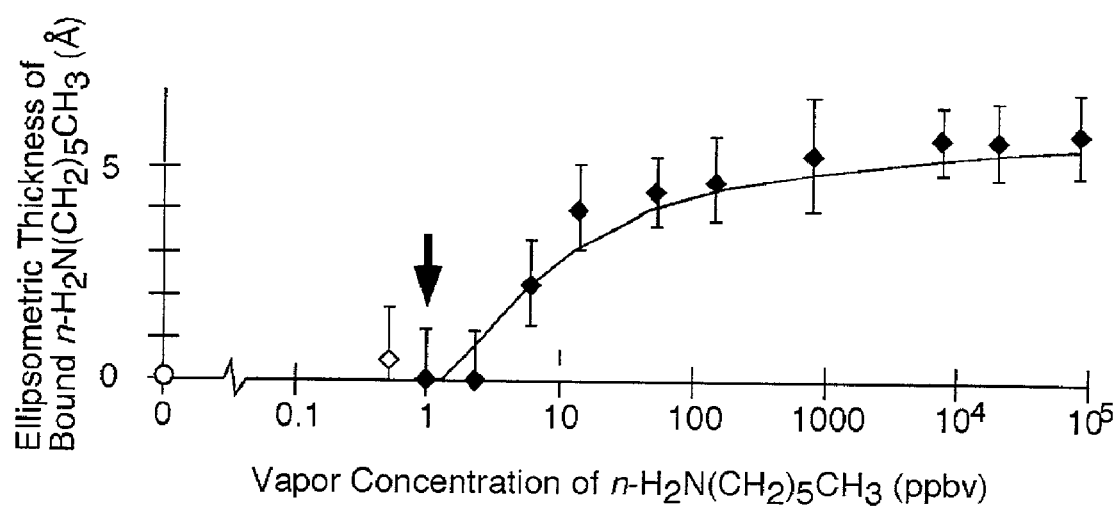
FIG. 7. is a graph showing the ellipsometric thickness of bound n-hexylamine as a function of the vapor concentration of n-hexylamine in ppbv for a SAM formed from 80% HOOC($CH_2$)SH and 20% $H_3C(CH_2)_{10}$SH with a nozzle spaced 1 mm from the SAM where ◆ indicates an in-plane orientation of 5CB that is perpendicular to the direction of gold deposition and ◇ indicates an in-plane orientation of 5CB that is parallel to the direction of gold deposition.

Because the above analysis suggests that the sensitivity of 5CB to the concentration of $H_2N(CH_2)_5CH_3$ in the vapor is determined by the rate of transport of $H_2N(CH_2)_5CH_3$ to the surface (diffusion-limited), studies were carried out in which the organoamine was convected to the SAM. By convecting $H_2N(CH_2)_5CH_3$ at 15 cm$^3$/min through a $\frac{1}{16}$" nozzle spaced either 1 or 2 mm from the SAM, transport limitations resulting from the concentration boundary layer could be significantly reduced. FIG. 6 shows the change in thickness of the SAM formed from $HOOC(CH_2)_{10}SH$ upon exposure to $H_2N(CH_2)_5CH_3$. On these surfaces, the in-plane transition of 5CB was observed to be triggered at 3–5 ppbv of $H_2N(CH_2)_5CH_3$ (1 mm spacings) and 100 ppbv to 200 ppbv of $H_2N(CH_2)_5CH_3$ (2 mm spacings) after 2 minutes of exposure to the nitrogen stream containing the organoamine. In both cases, the change in orientation of 5CB is driven by bound $H_2N(CH_2)_5CH_3$ with an ellipsometric thickness of about 1 Å. By forming a mixed SAM as described above and by introducing convection, the change in orientation of 5CB was shifted to approximately 1 ppbv of $H_2N(CH_2)_5CH_3$ as shown in FIG. 7. These results demonstrate that the sensitivity of devices for detecting the presence of compounds in a sample can be increased using mixed SAMs and/or convection to overcome mass transport limitations.

Selectivity of 5CB Supported on SAMs Containing Carboxylic Acid Functional Groups Whereas the above results establish that nematic phases of 5CB can be used to transduce $H_2N(CH_2)_5CH_3$ bound to SAMs formed from $HOOC(CH_2)_{10}SH$, they do not show the selectivity of the devices for the detection of organoamines. Studies were thus carried out to determine the selectivity of the detecting device prepared from alkanethiols containing carboxylic functional groups and 5CB using water and alcohols as both of these are known to be absorbed by carboxylic acid groups. These studies were conducted using the same mass transport conditions and gaseous samples containing $H_2N(CH_2)_5CH_3$, hexanes, ethanol, and water.

First, SAMs formed from $HOOC(CH_2)_{10}SH$ were exposed to hexanes in nitrogen at 100 ppmv and 200 ppmv. Whereas 100 ppbv to 200 ppbv of $H_2N(CH_2)_5CH_3$ triggered a change in the orientation of 5CB (FIG. 6), no change in the ellipsometric thickness or the orientations of 5CB was observed when the SAM was exposed to 100 or 200 ppmv hexanes. Second, SAMs formed from $HOOC(CH_2)_{10}SH$ were exposed, under the same transport conditions as used in hexanes, to a nitrogen stream doped with either 200 ppmv of ethanol or 200 ppmv of water. In both cases, no change in the ellipsometric thickness or the orientations of 5CB was observed after exposure to the nitrogen stream. These results collectively indicate that the orientations of 5CB supported on SAMs formed from $HOOC(CH_2)_{10}SH$ are selective to $H_2N(CH_2)_5CH_3$ over common compounds such as hexanes, water, and ethanol at concentrations greater than or equal to 200 ppmv.

Although the selectivity of the SAMs was excellent at low concentrations of hexanes, water, and ethanol, abnormally high swamping levels of non-specific vapors (saturated vapors) can trigger a response of the liquid crystal. For example, at 260,000 ppmv of hexanes (saturated vapor), an approximately 6 Å increase in the ellipsometric thickness of the SAM and a change in the orientation of the supported 5CB was observed upon exposure.

Spatial Imaging of n-Hexylamine Bound to SAMs

Figure 8A:
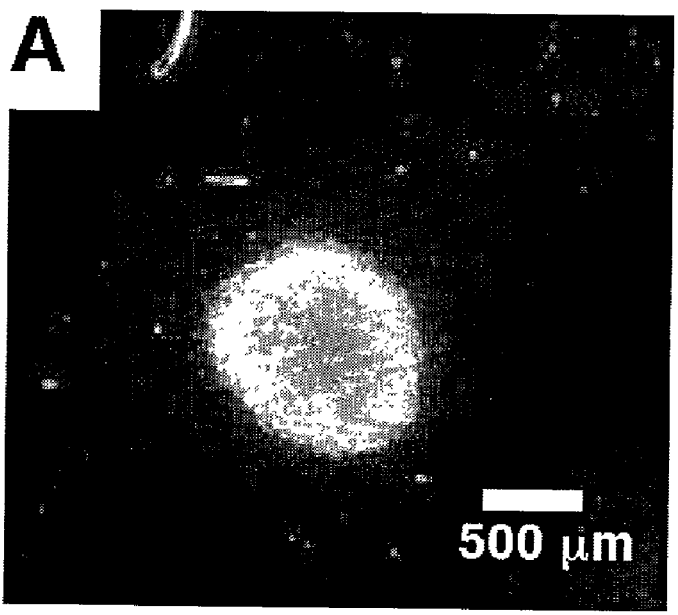
FIGS. 8A and 8B are images of the optical textures (parallel polars) of 5CB within optical cells formed with one surfaces supporting a SAM formed from $H_3C(CH_2)_{14}$SH and an opposing surface which is supporting a SAM containing alkanethiols with a carboxylic acid functional group The central lighter area was created by exposing the liquid crystal coated SAM to a nitrogen stream containing vapor concentration of 2 ppmv (FIG. 8A) and 50 ppbv (FIG. 8B) of n-hexylamine.
Figure 8B:
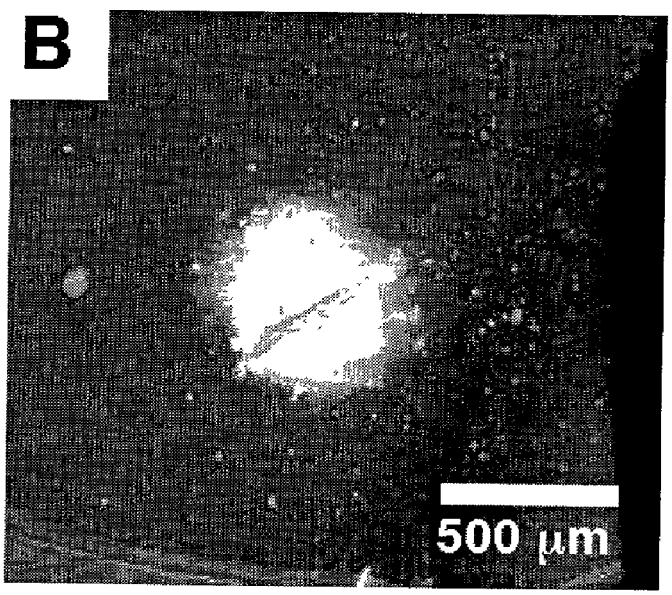

The above results demonstrate that 5CB can be used to selectively optically report the presence of an organoamine bound to carboxylic acid groups presented at the surface of SAMs. 5CB can also be used to image spatially localized areas of bound compounds on functional group-containing surfaces. Liquid crystal optical cells were manufactured by forming a SAM from $H_3C(CH_2)_{14}SH$ on one surface and a SAM from $HOOC(CH_2)_{10}SH$ on the opposing surface of the cell. Prior to assembling the cell, the entire surface of the SAM formed from $HOOC(CH_2)_{10}SH$ was pretreated at pH 3.2. This surface was subsequently exposed to a nitrogen stream doped with $H_2N(CH_2)_5CH_3$ that impacted the SAM after passing through a nozzle with a $\frac{1}{16}$" diameter. FIGS. 8A and 8B show the optical textures of a cell prepared in this manner using 2 ppmv (10 cm$^3$/min, 2 mm spacing) and 50 ppbv (15 cm$^3$/min, 1 mm spacing) of $H_2N(CH_2)_5CH_3$, respectively. When viewed through parallel polars, bright, circular regions were observed (FIGS. 8A and 8B) corresponding to regions of the surface that were exposed to $H_2N(CH_2)_5CH_3$. This result indicated that 5CB is anchored in the same azimuthal direction on both surfaces of the cell. The dark regions (those not exposed to $H_2N(CH_2)_5CH_3$), are caused by the presence of a twist distortion of about 90° within the 5CB. In short, binding of $H_2N(CH_2)_5CH_3$ to the immobilized carboxylic acid groups removed the twist distortion in the region of the optical cell where the nitrogen stream impacted the surface. In contrast, the twist distortion of 5CB remained in the regions not exposed to $H_2N(CH_2)_5CH_3$.

The shape of the area of bound $H_2N(CH_2)_5CH_3$ could be controlled by adjusting the angle of the nozzle with respect to the surface. For example, an oval region of an area where $H_2N(CH_2)_5CH_3$ was bound was obtained when $H_2N(CH_2)_5CH_3$ was deposited from a 1/16" outer diameter nozzle at a 15° oblique angle (2 mm spacing). Within the oval region where $H_2N(CH_2)_5CH_3$ was bound to the surface, the orientation of 5CB is perpendicular to the direction of gold deposition while outside this region, the orientation of 5CB is parallel to the direction of gold deposition.

Experimental Results Related to Organophosphorus Detection

Characterization of SAMs with Carboxylic Acids before and after Immersion in Ethanolic Solutions of $Cu(ClO_4)_2$ Surfaces having $Cu^{+2}$ carboxylate groups were prepared by immersing SAMs formed from $HOOC(CH_2)_{10}SH$ into ethanolic solutions between 0.1 μM to 100 mM of $Cu(ClO_4)_2$. In order to verify that copper was indeed complexed to the carboxylic acid groups of the alkanethiols of the SAM and to verify that this procedure did not deposit excess salts onto the surface, these SAMs were characterized before and after immersion into ethanolic solutions of $Cu(ClO_4)_2$ using ellipsometry and X-ray photoelectron spectroscopy (XPS).

Figure 9:
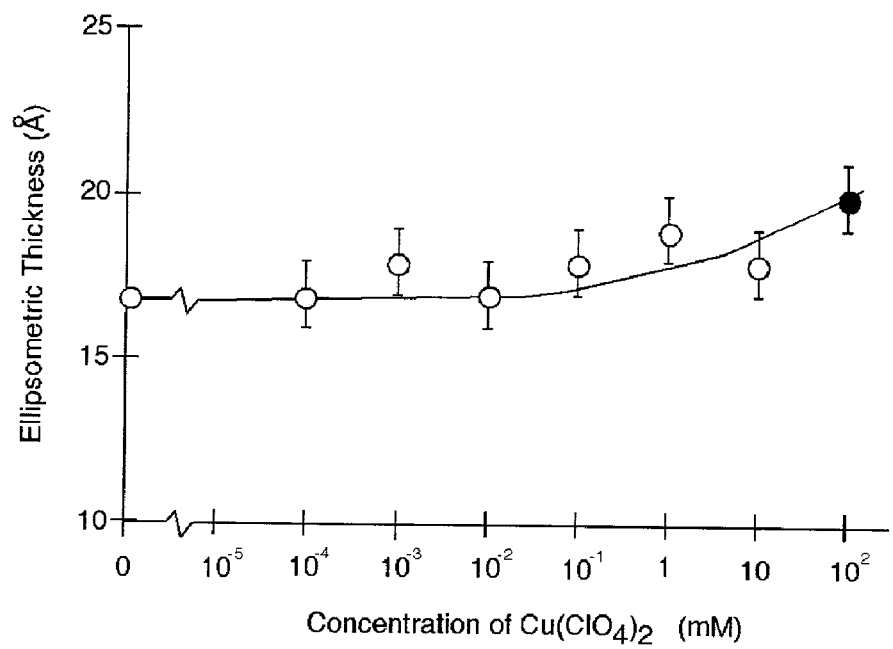
FIG. 9 is a graph showing the ellipsometric thickness of SAMs formed from HOOC($CH_2$)SH after immersion in ethanolic solutions of $Cu(ClO_4)_2$ where ● indicates homeotropic orientations within the optical cells and ○ indicates non-homeotropic orientations within the optical cells.

Ellipsometry results showed that the thickness of a SAM formed from $HOOC(CH_2)_{10}SH$ was 18±1 Å. FIG. 9 shows the effect on thicknesses of these SAMs after immersion for 5 minutes in ethanolic solutions with between 0.1 μM to 100 mM $Cu(ClO_4)_2$. No increase in the ellipsometric thickness was observed when solutions with a concentration up to 0.1 mM were used. A maximum ellipsometric thickness of 20±1 Å was measured when 100 mM $Cu(ClO_4)_2$ was used. Because a slight increase in the ellipsometric thickness was determined at a concentration of 100 mM, XPS was used to determine whether excess salts were deposited onto the SAM. Excess salts were found not to be deposited on these surfaces because elements such as chlorine or excessive oxygen that would originate from the perchlorate anion, and the underlying gold signal did not decrease systematically with increasing concentration of $Cu(ClO_4)_2$. Random variations of about 10% in the gold signal were all that was observed.

Figure 10:
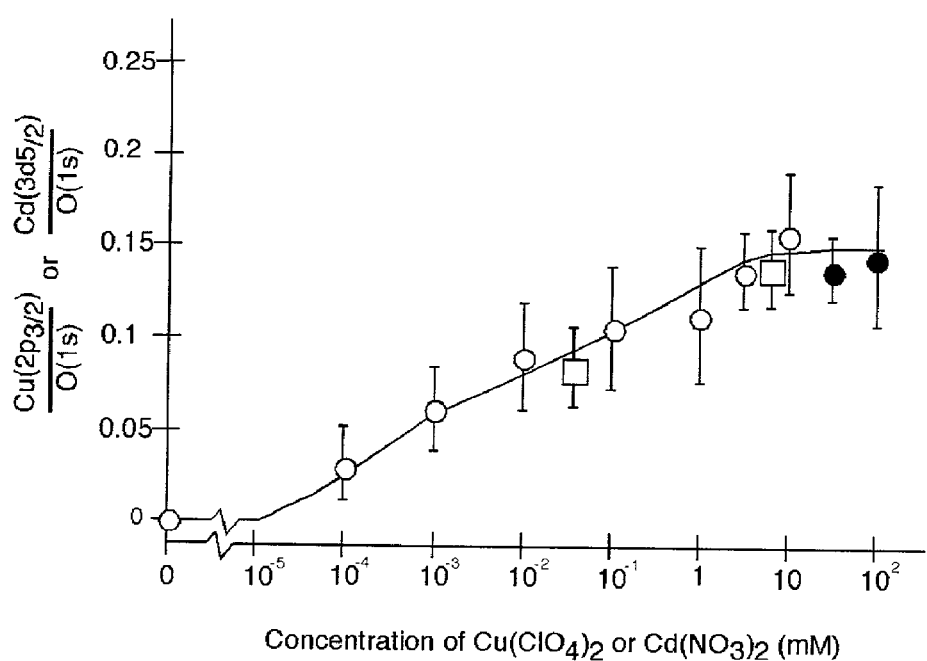
FIG. 10 is a graph showing the amount of copper and cadmium complexed on SAMs formed from HOOC($CH_2$)SH after immersion in ethanolic solutions of $Cu(ClO_4)_2$ or $Cd(NO_3)_2$ as measured by the ratio of $Cu(2p_{3/2})/O(1s)$ (○ and ●) and $Cd(3d_{5/2})/O(1s)$ (□) using XPS where ● indicates homeotropic orientations within the optical cells and ○ indicates non-homeotropic orientations within the optical cells.

XPS (FIG. 10) was also used to demonstrate that the areal density of $Cu^{+2}$ complexed to SAMs formed from $HOOC(CH_2)_{10}SH$ could be controlled by adjusting the concentration of the copper ion upon immersion into ethanolic solutions of $Cu(ClO_4)_2$. As shown in FIG. 10, the ratio of $Cu(2p_{3/2})/O(1s)$ between 0 and 0.15 could be controlled by adjusting the concentration of $Cu(ClO_4)_2$ in the ethanol. A surface conversion to plateau was observed at 0.15 of 10 mM of $Cu(ClO_4)_2$. In summary, the measurements above, when combined, lead us to the conclusion that experimental procedures based on the immersion and withdrawal of SAMs from ethanolic solutions of $Cu(ClO_4)_2$ can be used to prepare SAMs presenting $Cu^{+2}$ carboxylates at the surface of obliquely deposited films of gold. Furthermore, these SAMs do not support excess salt over the concentration range tested.

Orientations of Nematic 5CB Supported on SAMs with Metal Carboxylates

The orientations of 5CB supported on SAMs formed from $HOOC(CH_2)_{10}SH$ complexed with increasing areal densities of copper were measured. The orientations of 5CB were observed in optical cells (thickness of about 4 μm) fabricated with gold films supporting SAMs. The gold films were aligned such that the direction of deposition of the gold was parallel within the two surfaces. 5CB was oriented planar to the surface and parallel to the direction of gold deposition on SAMs formed from $HOOC(CH_2)_{10}SH$. As the areal density of copper complexed on the surface increased, the texture of 5CB became increasingly non-uniform. While the in-plane orientation of 5CB was parallel to the direction of gold deposition, when using 0.1 μM $Cu(ClO_4)_2$, the growth of a marbled texture with domains ranging in size from about 10 μm to 20 μm when using 1 μM of $Cu(ClO_4)_2$, about 20 μm to 50 μm when using 10 μM of $Cu(ClO_4)_2$, and about 40 μm to 80 μm when using at 0.1 mM of $Cu(ClO_4)_2$. For surfaces pretreated in 1 mM solutions, no regions exhibiting uniform orientation of liquid crystal were observed and the average domain of liquid crystal was larger than 100 μm. For surfaces pretreated using 10 mM of $Cu(ClO_4)_2$, schlieren textures were observed (containing +/−¼ defects) and interpreted to indicate non-uniform, tilted orientations of 5CB. Finally, near-homeotropic alignment was observed for 5CB on surfaces exposed to 30 mM $Cu(ClO_4)_2$.

Spatial Patterning of Copper within SAMs with Copper Carboxylates

As described above, 5CB can be used to optically detect the complexation of copper to carboxylic acid functional groups of alkanethiols immobilized on surfaces such as obliquely deposited gold surfaces on glass supports. 5CB can also be used to spatially image regions of surfaces patterned with carboxylic acid groups and $Cu^{+2}$ complexed to carboxylic acid groups. The ability to spatially resolve these species by preparing liquid crystal cells from SAMs formed from $HOOC(CH_2)_{10}SH$ has also been established. Prior to assembling an optical cell, the SAMs were dipped half-way into ethanolic solutions of either 1 mM or 100 mM $Cu(ClO_4)_2$ for 5 minutes and then aligned with the surfaces facing inwards. When viewed through crossed polars at maximum extinction, the region with the COOH functional group that had not contacted the metal appears dark due to the extinction of light transmitted through the cell by the analyzer. This result and others indicates that 5CB is anchored in this region without the metal carboxylate in the same azimuthal direction on both surfaces of the cell. In the region with the $Cu^{+2}$ complexed to the carboxylic acid, light was transmitted through cross polars (obtained when using the 1 mM solution of $Cu(ClO_4)_2$), reflecting the presence of copper bound to the surface or light was uniformly extinguished through cross polars, reflecting homeotropic alignment of 5CB in this region of the cell (obtained when using the 100 mM solution of $CU(ClO_4)_2$). The optical texture of the same cells viewed at maximum transmission (cross polars) clearly revealed regions of the surface of the cell that are complexed with $Cu^{+2}$.

Interaction of 5CB and SAMs with Copper Carboxylate Functional Groups

Because solvents containing the nitrile functionality (such as acetonitrile and benzonitrile) may coordinate to $Cu^{+2}$ in the presence of water, it was initially surmised that the orientational behavior of 5CB was governed by a weak complex between the nitrile moiety of the 5CB and the $Cu^{+2}$ on the surface. This proposition was tested using two experimental approaches. First, the orientations of n-(p methoxybenzylidene)-p-(n-butyl-aniline) (MBBA) on SAMs formed from $HOOC(CH_2)_{10}SH$ pretreated with 1 mM or 100 mM of $Cu(ClO_4)_2$ was determined. MBBA does not possess the nitrile functionality and thus cannot coordinate with the copper in the same way 5CB and other nitrile-containing liquid crystals can. MBBA was determined to orient in the plane of the SAM in an azimuthal direction that was perpendicular to the direction of gold deposition.

Second, the orientation of 5CB on SAMs formed from $HOOC(CH_2)_{10}SH$ pretreated within ethanolic solutions of $Cd(NO_3)_2$ was determined. It is known that cadmium complexes to the carboxylic acid functional group, but forms weaker complexes with the nitrile group than does copper. Prior to measuring the orientation of liquid crystals on these surfaces, the SAMs were characterized before and after immersion in ethanolic solutions of $Cd(NO_3)_2$ because it was thought that excess salts may deposit on these SAMs on immersion into the cadmium salt solution. XPS did not show any excess salts on the surface especially from compounds containing nitrogen (originating from the nitrate anion). Next, the areal density of Cd complexed onto these SAMs from ethanolic solutions of $Cd(NO_3)_2$ of 40 µm and 4 mM was measured. The azimuthal orientation of 5CB was determined to be perpendicular to the direction of gold deposition for SAMs immersed in ethanolic solutions of $Cd(NO_3)_2$ between 1 µm to 5 mM. The orientation remained invariant as the areal density of cadmium increased on the surface (as measured by XPS-See FIG. 10). In fact, the azimuthal orientation of 5CB (and MBBA) was perpendicular to the direction of gold deposition for all non-complex forming metals (Cd and all alkali metals e.g. Li, Na, K, Rb, Cs). These results, when combined, support the proposition that a weak bond between the nitrile-group of 5CB and the $Cu^{+2}$ influences the orientation of 5CB on surfaces presenting $Cu^{+2}$ carboxylate functional groups. In addition, exposing SAMs to ethanolic solutions containing different concentrations of $Cu(ClO_4)_2$ allows for the manipulation of this interaction and the tuning of the orientation of the nematic 5CB.

Influence of Dimethyl Methylphosphonate on the Orientation of 5CB

Dimethyl methylphosphonate forms a complex with metal carboxylates such as $Cu^{+2}$ carboxylates and displaces the nitrile group of 5CB from its complex with $Cu^{+2}$ prior to exposure to the organophosphorus compound. The displacement of the liquid crystal drives a real-time reorientation of the liquid crystal supported on the surface which allows for the detection of organophosphorus compounds.

The optical textures of thin films of 5CB (about 4 µm thickness) formed by spin coating about 10 µl of 5CB upon a SAM formed from $HOOC(CH_2)_{10}SH$ previously immersed in a 100 mM $Cu(ClO_4)_2$ ethanol solution for 5 minutes were examined. The intensity of light transmitted through the film did not vary significantly when the sample was rotated between crossed polars as shown for one position. Additionally, the conoscopic figure indicated that 5CB was oriented in a near-homeotropic alignment throughout the film The uniform orientation of 5CB making up the film results from homeotropic orientation of 5CB at the 5CB-air interface and the near-homeotropic orientation at the 5CB-copper/SAM interface. This orientation was found to be stable for over 12 hours under ambient conditions.

When the above described film of 5CB was exposed to 900 ppmv of $(H_3CO)_2P(=O)CH_3$, the intensity of light passing through the film modulated when the sample was rotated between crossed polars. This resulted because the binding of the organophosphonate at the copper/SAM interface induced a uniform, tilted orientation of 5CB. Because the orientation of 5CB is not the same at both surfaces, the out-of-plane orientations of 5CB gradually changes over the thickness of the nematic film. The out-of-plane orientation of 5CB (as determined by conoscopy) leads to an apparent tilt that averages the local tilt over the thickness of the film of liquid crystal. The apparent tilt of 5CB depended upon the time of exposure of the nematic film to the dimethyl methylphosphonate. For example, after about 1 minute, an about 10° apparent tilt from the normal was measured, and after about 5 minutes, an about 20° apparent tilt was measured. The in-plane direction of the tilt of the 5CB was parallel to the direction of gold deposition alignment as determined using interference colors. Finally, the tilt induced within the films was reversible such that when films were removed from exposure to samples containing $(H_3CO)_2P(=O)CH_3$, the 5CB reverted to its original homeotropic orientation.

No detectable changes in the orientation within films of 5CB supported on SAMs formed from $H_3C(CH_2)_{11}SH$ (for 5CB confined within optical cells), $HO(CH_2)_{11}SH$, $HOOC(CH_2)_{10}SH$, and $Na^+$ $^-OOC(CH_2)_{10}SH$ occurred upon exposure to 900 ppmv $(H_3CO)_2P(=O)CH_3$.

Sensitivity and Response Time of 5CB to Dimethyl Methylphosphonate

As noted above, SAMs that include $Cu^{+2}$ carboxylates and 5CB exhibit a change in the orientation of the liquid crystal when exposed to samples containing $(H_3CO)_2P(=O)CH_3$, and the orientation of 5CB changes from homeotropic to a uniform, tilted orientation on exposure to the organophosphorus compound. This transition was easily transduced using polarized light. The response time and sensitivity of the orientations of 5CB supported on SAMs formed from $HOOC(CH_2)_{10}SH$ pretreated in a 100 mM $Cu(ClO_4)_2$ solution was measured as a function of the bulk vapor concentration of $(H_3CO)_2P(=O)CH_3$.

Figure 11A:
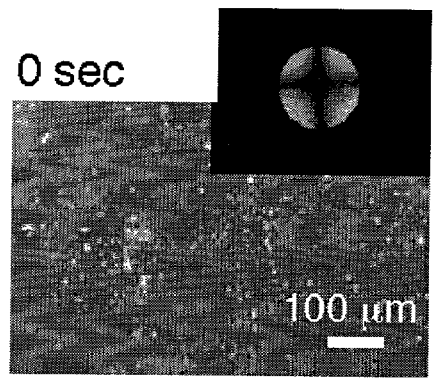
FIGS. 11A through 11F are optical images (taken between cross polars) showing the time-dependent change in orientation of a film of nematic 5CB (thickness of about 4 μm) spin-coated on a SAM formed from HOOC($CH_2)_{10}$SH pretreated by immersion in an ethanolic solution of 100 mM $Cu(ClO_4)_2$ upon exposure to 500 ppbv dimethyl methylphosphonate convected through a obliquely cut nozzle 3 mm from the surface of the film.
Figure 11B:
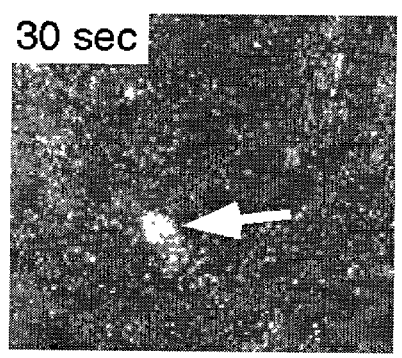
Figure 11C:
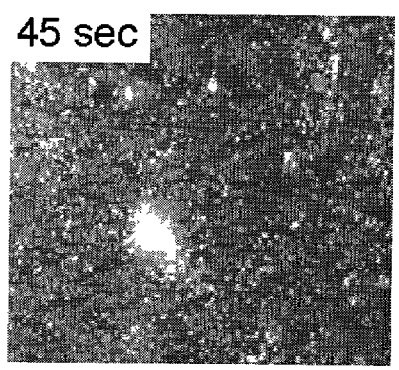
Figure 11D:
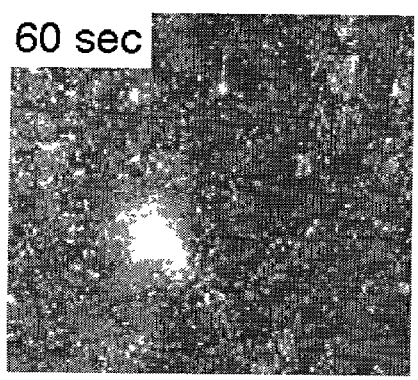
Figure 11E:
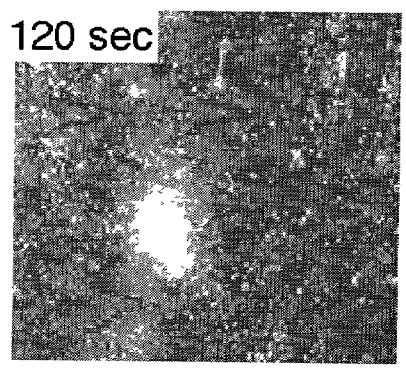
Figure 11F:
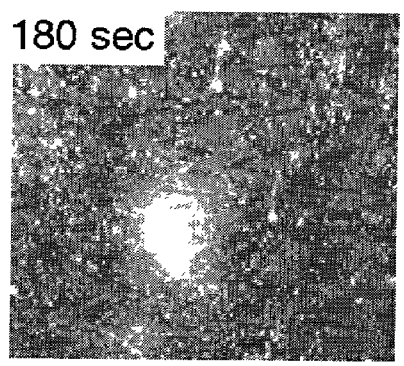

In order to circumvent transport limitations of the analyte to the surface of the liquid crystal, 15 cm³/min of nitrogen containing vapor concentrations of $(H_3CO)_2P(=O)CH_3$ that were between 20 to 900,000 ppbv was convected to the film of 5CB through a horizontal glass tube positioned 2 or 3 mm from the surface of the film of 5CB. FIGS. 11A through 11F show the spatial binding of $(H_3CO)_2P(=O)CH_3$ as transduced through the change in orientation of 5CB (between cross-polars) from near homeotropic-to-tilted within films exposed to vapor concentrations of $(H_3CO)_2P(=O)CH_3$ at 500 ppbv (3 mm spacing) using a glass tube. The spatial region (white area) transduced by the 5CB originates near the center of the image as shown by the arrow in the frame captured at 30 seconds after exposure (FIG. 11B). This area expanded radially with exposure time. The "sparkles" in the image (at t=0 sec) are due to regions within the nematic film that are not oriented homeotropically. These domains are areas that contain different "apparent" out-of-plane orientations.

An enhancement in the quality of the images was obtained by subtracting the intensity of transmitted light within the film prior to the binding of $(H_3CO)_2P(=O)CH_3$. While both cases (20 ppbv and 500 ppbv of the dialkyl alkylphosphonate) demonstrated the ability to spatially image regions that bind $(H_3CO)_2P(=O)CH_3$ with time, the type of tip used for dispensing the $(H_3CO)_2P(=O)CH_3$ directly affects the shape of the plume of $(H_3CO)_2P(=O)CH_3$ that was imaged using 5CB. Whereas using a blunt tube (20 ppbv) resulted in a plume that distributed $(H_3CO)_2P(=O)CH_3$ over distances of millimeters, the obliquely grounded glass tube directed $(H_3CO)_2P(=O)CH_3$ over length scales of hundreds of micrometers.

The effect of concentration and transport of $(H_3CO)_2P(=O)CH_3$ from a horizontal blunt tube was also quantitatively investigated at two different spacings, (2 mm and 3 mm) by measuring the luminance or optical output during exposure to vapor concentrations of dimethyl methylphosphonate.

Figure 12:
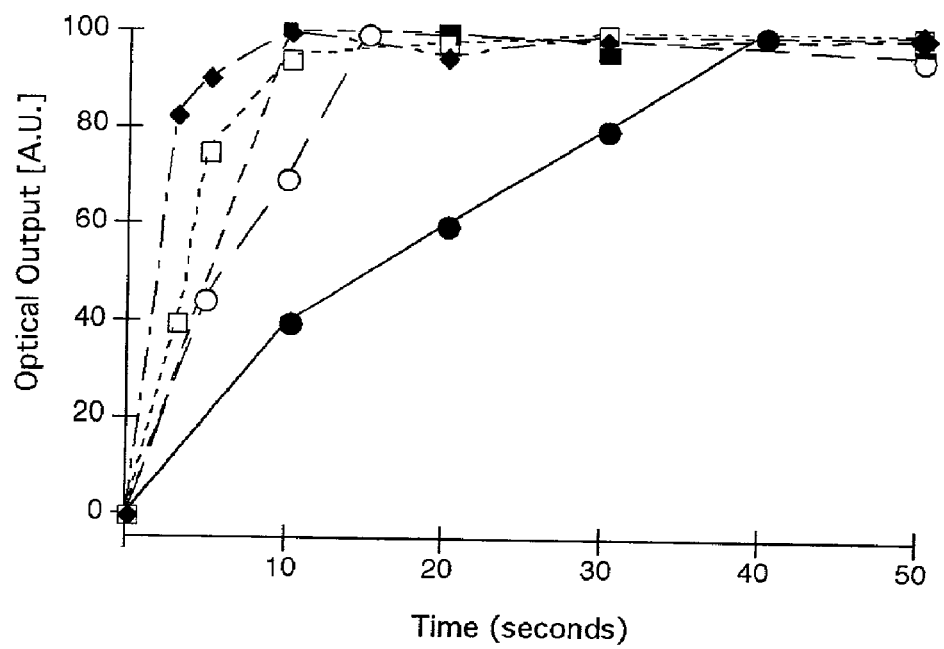
FIG. 12 is a graph showing the average luminance of a film of 5CB (thickness of about 4 μm) on a SAM formed from HOOC($CH_2)_{10}$SH that was pretreated by immersion in an ethanolic solution of 100 mM $Cu(ClO_4)_2$ after exposure to dimethyl methylphosphonate from a nozzle located at 2 mm above the surface at concentrations of (●) 20 ppbv, (○) 85 ppbv, (□) 1 ppmv and (◆) 2 ppmv.
Figure 13:
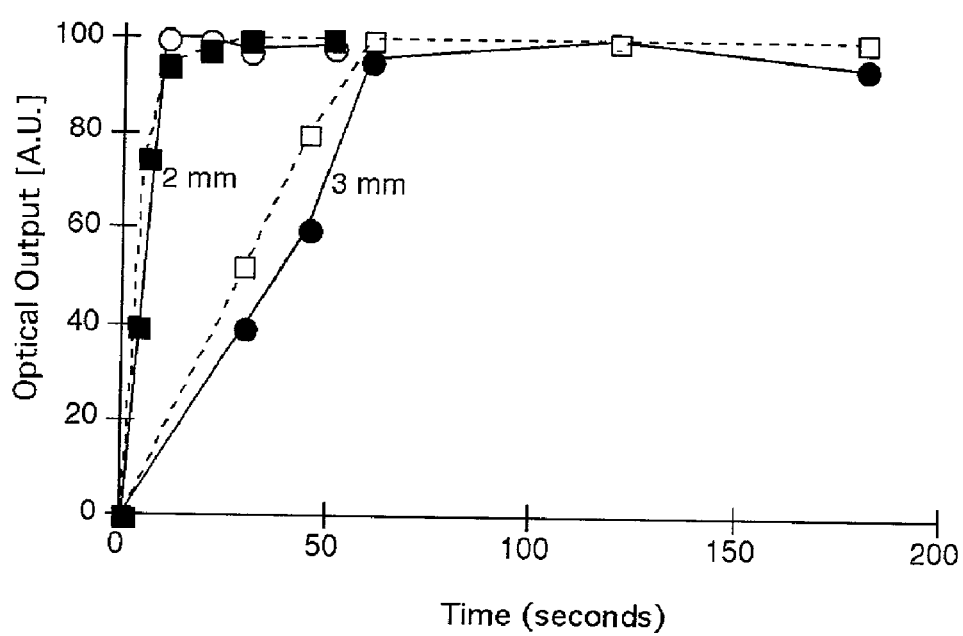
FIG. 13 is a graph showing the luminance of films of 5CB after exposure to dimethyl methylphosphonate convected from nozzles located 2 mm (filled symbols) and 3 mm (open symbols) from the surface for concentrations of dimethyl methylphosphonate of 200 ppbv (● and ○) or 1 ppmv (■ and □).

FIGS. 12 and 13 quantify the change in orientation of 5CB through the luminance measured upon exposure of the liquid crystal to vapor concentrations of $(H_3CO)_2P(=O)CH_3$ from 20 ppbv to 2,000 ppbv at a 2 mm spacing during exposure to $(H_3CO)_2P(=O)CH_3$. The initial response of 5CB decreased from about 5 sec (from 85 ppbv to 2,000 ppbv) to about 10 sec (at 20 ppbv) as shown in FIG. 12. In FIG. 13, the response at two different spacings (2 and 3 mm) of the nozzle from the surface of the film is shown for vapor concentrations of (H3CO)2POCH3 of 200 ppbv and 1,000 ppbv. These results demonstrate that the spacing of the nozzle from the surface of the film of 5CB influences the response time of 5CB to $(H_3CO)_2P(=O)CH_3$.

Figure 14:
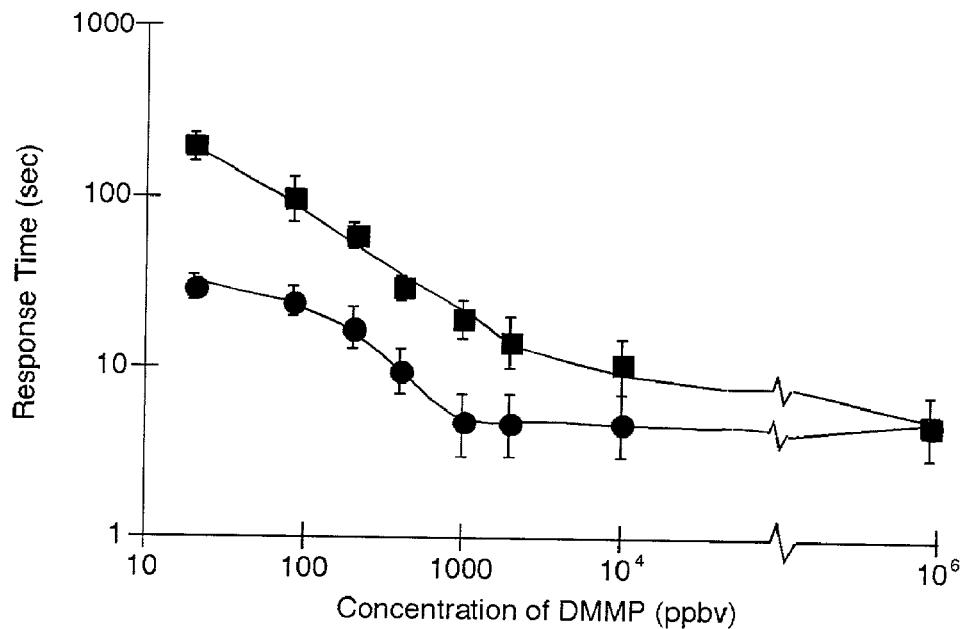
FIG. 14 is a graph showing the response times of films of 5CB (thickness of about 4 μm) as function of the concentration of dimethyl methylphosphonate as observed at luminances of between 40% and 50% caused by the change in orientation of the 5CB supported on SAMs with $Cu^{+2}$ carboxylates after exposure to dimethyl methylphosphonate convected to the surface at spacing of 2 mm (●) and 3 mm (○) from the surface of the film at concentrations of between 20 ppbv and 900 ppmv.

FIG. 14 is a plot of the time taken for the luminosity of the liquid crystal to reach 40% to 50% as a function of the vapor concentration of $(H_3CO)_2P(=O)CH_3$. As shown in FIG. 14, a near-constant response time was observed for all vapor concentrations of $(H_3CO)_2P(=O)CH_3$ greater than 1,000 ppbv, and nozzle spacings. Below 1000 ppbv, a steady increase in the response time of the film was seen. A longer overall response time was observed for a nozzle spaced 3 mm from the surface of the film as compared to a nozzle spaced at 2 mm.

Reversibility of Binding of Dialkyl Alkylphosphonates

The above results show that optical cells prepared from surfaces comprising metal carboxylates and 5CB provide a high level of sensitivity to dialkyl alkylphosphonates. The change in the orientation of 5CB induced by exposure to $(H_3CO)_2P(=O)CH_3$ is reversible. FIG. 15 illustrates the response of the orientations of 5CB, as measured through the luminance (between cross polars), for a nozzle spaced 3 mm from the surface of the film of 5CB and a vapor concentration of 10 ppmv of $(H_3CO)_2P(=O)CH_3$. For samples exhibiting a minimum in the luminance, 5CB is in its original homeotropic orientation. Upon addition of $(H_3CO)_2P(=O)CH_3$ to the nitrogen stream at 50 seconds, the luminance increased from 0 to saturation at t=100 seconds. Upon removal of the $(H_3CO)_2P(=O)CH_3$, the orientation of 5CB reverted back to the preexposure orientation as observed by the minimum in the optical response (10 A.U. to 15 A.U.). When $(H_3CO)_2P(=O)CH_3$ was reintroduced into the nitrogen stream, the luminance saturated over 50 seconds.

Sensitivity and Selectivity of SAMs with Metal Carboxylates to other Compounds The selectivity of the SAMs possessing $Cu^{+2}$ carboxylate functional groups SAMs and 5CB was examined by exposing the film (under the same mass transport conditions) to vapors of $(H_3CO)_2P(=O)CH_3$, hexanes, acetone, ethanol, and water.

The selectivity of SAMs with copper carboxylate functional groups and 5CB was first tested by exposing such surfaces to hexanes in nitrogen at 300 ppmv and 3,000 ppmv and comparing to the results obtained with $(H_3CO)_2P(=O)CH_3$. While <20 ppbv of $(H_3CO)_2P(=O)CH_3$ triggered a change in the orientation of 5CB, at 300 ppmv and 3,000 ppmv of hexanes, no observable change in the alignment of 5CB could be detected. The surfaces of the SAMs was then tested under the same transport conditions by exposing them to 1000 ppmv of acetone. Upon exposure to acetone, the orientations of 5CB within the film remained homeotropic and no change was detected. Finally, the film of 5CB on the SAM was exposed to 300 ppmv of ethanol and 300 ppmv of water. Exposure to the ethanol and the water resulted in no change in the orientation of the liquid crystal. These results indicate that SAMs formed from $HOOC(CH_2)_{10}SH$ and copper, when combined with the use of 5CB, are selective towards organophosphorus compounds such as organophosphonates.

Summary of Experimental Results

The competitive binding of a molecule forming a liquid crystal and a targeted analyte or compound to a common molecular receptor or functional group presented at a solid surface such as a self-assembled monolayer deposited on a support and possessing nanometer-scale topography, triggers an easily visualized surface-driven change in the orientation of a film of liquid crystal usually of micrometer thickness. Diffusion of the targeted analyte from a gaseous sample such as the atmosphere to a surface-immobilized receptor, such as a functional group on a thiol, across the film of liquid crystal has been observed to occur fast (occurs in seconds). Additionally, the competitive interaction of the compound and the moiety of the liquid crystal with the functional group on the surface provides a high level of tolerance to non-targeted species such as, but not limited to, water, ethanol, acetone and hexanes. Systems that provide parts-per-billion (by volume) sensitivity to organoamine and organophosphorus compounds have been constructed, and their use for imaging of spatial gradients in concentration has been shown.

For detection of organoamines, carboxylic acid (—COOH) groups were used as the molecular receptors or functional groups of the alkanethiol, and 4-cyano-4'-pentylbiphenyl (5CB) was used as the liquid crystal. Whereas the nitrile group of 5CB can form hydrogen bonds and thus reversibly interact with a —COOH group (bond strength 10 kJ/mol to 40 kJ/mol), an organoamine reversibly interacts with a —COOH functional group through a stronger acid-base interaction (>70 kJ/mol). Ultra-thin gold films were prepared with a nanometer-scale topography and with protruding surface-immobilized —COOH groups. The topography of the such surfaces may be idealized as a nanometer-scale corrugation with an amplitude of about 1 nm to 2 nm and a wavelength of 10 nm to 30 nm. When contacted with such a surface, 5CB spontaneously assumed an orientation that was parallel to the surface and perpendicular to (across) the nanometer-scale corrugation, consistent with the influence of the hydrogen bonding of the nitrile group of the mesogen (5CB) to the surface-immobilized (—COOH) functional groups. In contrast, exposure of the acidic surface to a vapor of an organoamine such as n-hexylamine ($H_2N(CH_2)_5CH_3$) before or after contact with 5CB caused a film of nematic 5CB to assume an orientation that was visually distinct.

Using polarized light microscopy, the surface-induced orientation of the 5CB after exposure to hexylamine was determined to be parallel to or along the nanometer-scale corrugation of the surface. In contrast, exposure of 5CB supported on a surface presenting methyl groups rather than carboxylic acid groups to n-hexylamine did not lead to any observable change in the orientation of 5CB. Similarly, exposure of 5CB supported on a surface comprising —COOH functional groups to water vapor, ethanol, hexanes and dimethyl methylphosphonate (($H_3CO)_2POCH_3$) did not trigger a measurable change in the orientation of 5CB. It is concluded that hexylamine competitively displaces 5CB by reversibly interacting with the carboxylic acid functional group of the alkanethiol of the self-assembled monolayer and thus interrupts the reversible hydrogen bond interaction between the carboxylic acid functional group of the alkanethiol and the nitrile group of the 5CB. Competitive displacement of the liquid crystal by the hexylamine results in an observable change in the orientation of the liquid crystal on the surface allowing detection of the hexylamine. Because the acid-base interaction of the carboxylic acid and amine has a slow off rate, the sensitivity of the liquid crystal to bound hexylamine was determined by measuring the amount of hexylamine bound to the acidic surface prior to placement of 5CB on the surface. It was determined that the change in the orientation of 5CB is triggered by amounts of bound hexylamine that possessed optical thicknesses below the detection limits of ellipsometry (ellipsometric thickness <1 Å). Exposure of these surfaces to parts-per-billion concentrations of hexylamine for two minute periods resulted in measurable and detectable changes in the orientation of the 5CB.

When the bound —COOH groups were pretreated by immersion in ethanolic solutions containing 100 mM $Cu^{2+}$, $Cu^{2+}$ was incorporated into the surfaces by formation of a metal carboxylate complex causing micrometer-thick 5CB spin coated films to adopt an orientation that was perpendicular to the surface. Mesogens not possessing a nitrile group (such as nematic phases of n-(p-methoxybenzylidene) did not orient perpendicular to surfaces presenting $Cu^{2+}$. Similarly, the incorporation of $Cd^{2+}$ into surfaces presenting carboxylic acid functional groups did not cause 5CB to assume a perpendicular orientation, consistent with the weaker binding of nitrile groups to $Cd^{2+}$ as opposed to $Cu^{2+}$. It was thus concluded that complexation of the nitrile groups of 5CB with $Cu^{2+}$ presented at the surface as a metal carboxylate gave rise to the perpendicular orientation of 5CB on the surface. Exposure of the perpendicularly oriented film of 5CB to 300 ppm of water, acetone, hexanes, or ethanol did not change the optical appearance of the film of 5CB. However, exposure of the surface containing the $Cu^{+2}$ carboxylate metal complex to ppm to ppb concentrations of ($H_3CO)_2P(=O)CH_3$ resulted in an easily visualized change in the orientation of the liquid crystal. By using polarized light microscopy and interferometry, the change in orientation of the liquid crystal was determined to be a tilt (10° to 20°) of the liquid crystal away from the normal of the surface in an azimuthal direction that is perpendicular to the nanometer-scale corrugations on the surface.

It was concluded that the competitive binding of ($H_3CO)_2P(=O)CH_3$ to the $Cu^{2+}$ of the metal carboxylate hosted at the surface displaced 5CB from the liquid crystals' weak complex with $Cu^{2+}$ thereby triggering the readily observable change in the orientation of the liquid crystal. The liquid crystal reverted to its original perpendicular orientation when re-exposed to an atmosphere free of ($H_3CO)_2P(=O)CH_3$ indicating the reversible nature of the interaction between the copper carboxylate and the dimethyl methylphosphonate. Exposure to about 20 ppbv concentrations (limit of dilution of the experimental set-up) of ($H_3CO)_2P(=O)CH_3$ for about 20 seconds resulted in easily observed changes in the liquid crystal of the device.

Two approaches can be used to quantify either cumulative or instantaneous exposure to targeted analytes or compounds. First, measurement of the spatial extent of diffusion of an organoamine such as hexylamine laterally across a confined film of liquid crystal can be used to indicate cumulative exposure to time-varying concentrations of the analyte. Second, surfaces may be designed that trigger a dynamic response of the liquid crystal that depends upon the instantaneous concentration of a targeted analyte. Devices such as badges and other sensors may thus be used in various applications to show the presence of a compound in a sample or area at a specific time or over a continues period of time. The devices may also be employed to determine the amount of useful life remaining in protective equipment such as gas masks and other protective clothing.

The above results demonstrate that surfaces with nanometer-scale topography and receptor or functional group chemistry may be designed such that competitive interactions of mesogens and targeted analytes or compounds, such as, but not limited to, organophosphonates and organoamines, to surface-immobilized functional groups are amplified into chemically-specific, surface-driven orientational transitions in liquid crystals. Because a wide variety of metal ions may be patterned on surfaces within areas possessing micrometer-scale dimensions, and because liquid crystals may be used to image surfaces on similar spatial scales, the general approach offers the possibility of rapidly screening for molecular receptors or combinations of molecular receptors for a range of targeted environmental agents as well as providing a basis of measurement tools suitable for highly-multiplexed determinations of personal exposure to a wide range of chemical environments. By proper selection of functional group, reactions with the compound to be detected may be made reversible or irreversible such that devices may be manufactured as personal dosimeters for determining either chronic or acute exposure to the compound. Such devices may take the form of badges or other items that may be worn by individuals in environments where the compound may be present. Furthermore, microcontact printing allows for the manufacture of devices which allows for ready detection of compounds in a sample. Finally, devices may be provided with a pump that convects a sample over a liquid crystal in the device such that lower levels (e.g. ppb) of a compound in a sample may be detected in a rapid and simple manner.

It is understood that the invention is not limited to the embodiments set forth herein for illustration, but embraces all such forms thereof as come within the scope of the claims.

What is claimed is:

1. A device for detecting the presence of a compound in a sample, comprising:
   (a) a substrate comprising a support with a metallized top surface;

(b) a self-assembled monolayer comprising an alkanethiol attached to the metallized top surface of the substrate, the alkanethiol having a functional group that reversibly or irreversibly interacts with the compound, wherein the functional group comprises a metal selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu; and (c) a liquid crystal disposed on a top surface of the self-assembled monolayer opposite the side of the self-assembled monolayer attached to the metallized top surface of the substrate, the liquid crystal comprising a moiety that interacts with the functional group of the alkanethiol, wherein when the compound is present in a sample that contacts the self-assembled monolayer, the orientation of the liquid crystal disposed on the self-assembled monolayer is altered.

2. The device of claim 1, wherein the functional group of the alkanethiol is a metal carboxylate.

3. The device of claim 1, wherein the liquid crystal is a nematic liquid crystal.

4. The device of claim 1, wherein the liquid crystal comprises a nitrile group, and the functional group of the alkanethiol is a metal carboxylate.

5. The device of claim 1, wherein the liquid crystal is 4-cyano-4'-pentylbiphenyl.

6. The device of claim 1, wherein the alkanethiol has the formula $HS(CH_2)_nCO_2H$ and n is an integer selected from the group consisting of 1, 2, 3, 4, 5, 6, 7, 8, 9, 10, 11, 12, 13, 14, 15, 16, 17, 18, 19, and 20.

7. The device of claim 6, wherein n is 10.

8. The device of claim 1, wherein the metallized top surface of the substrate comprises a metal selected from the group consisting of gold and silver.

9. The device of claim 1, wherein the metallized top surface comprises gold obliquely deposited at an angle of from about 30° to about 60° to a top surface of the support.

10. The device of claim 9, wherein the gold is obliquely deposited at an angle of about 50° to the top surface of the support.

11. The device of claim 9, wherein the gold is deposited over a layer of an adhesion promoting material.

12. The device of claim 1, wherein the support is a glass plate or a glass slide.

13. The device of claim 1, wherein the uniformity of the orientation of the liquid crystal on the self-assembled monolayer increases when the self-assembled monolayer is exposed to the sample and the sample includes the compound.

14. An optical cell, comprising:
(a) the device of claim 1; and
(b) a second surface that uniformly aligns the liquid crystal when the liquid crystal contacts the second surface, wherein the second surface contacts a first surface of the liquid crystal which is opposite a second surface of the liquid crystal that contacts the self-assembled monolayer of the device.

15. A method for detecting the presence of a compound in a sample, comprising:
(a) contacting a device for detecting the presence of a compound in a sample with the sample, wherein the device for detecting the presence of the compound in a sample comprises:
(i) a substrate comprising a support having a metallized top surface; and
(ii) a self-assembled monolayer comprising a first alkanethiol attached to the metallized top surface of the substrate, the alkanethiol comprising an alkanethiol having a functional group that reversibly or irreversibly interacts with the compound, wherein the functional group comprises a metal selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu;

(b) disposing a liquid crystal on a top surface of the self-assembled monolayer of the substrate, the liquid crystal having a moiety that interacts with the functional group of the alkanethiol; and (c) determining whether the orientation of the liquid crystal on the self-assembled monolayer changes after the device contacts the sample.

16. The method of claim 15, wherein the liquid crystal is disposed on the top surface of the self-assembled monolayer of the substrate after the device contacts the sample.

17. The method of claim 15, wherein the liquid crystal is disposed on the top surface of the self-assembled monolayer before the device contacts the sample.

18. The method of claim 15, wherein the functional group of the alkanethiol is a metal carboxylate.

19. The method of claim 15, wherein the liquid crystal is a nematic liquid crystal.

20. The method of claim 15, wherein the liquid crystal comprises a nitrile group, and the functional group of the alkanethiol is a metal carboxylate.

21. The method of claim 15, wherein the liquid crystal is 4-cyano-4'-pentylbiphenyl.

22. The method of claim 15, wherein the alkanethiol has the formula $HS(CH_2)_nCO_2H$ and n is an integer selected from the group consisting of 1, 2, 3, 4, 5, 6, 7, 8, 9, 10, 11, 12, 13, 14, 15, 16, 17, 18, 19, and 20.

23. The method of claim 22, wherein n is 10.

24. The method of claim 15, wherein the metallized top surface of the substrate comprises a metal selected from the group consisting of gold and silver.

25. The method of claim 15, wherein the metallized top surface of the substrate comprises gold and the gold is obliquely deposited at an angle of from about 30° to about 60° to a top surface of the support.

26. The method of claim 25, wherein the gold is obliquely deposited at an angle of about 50° to the top surface of the support.

27. The method of claim 25, wherein the gold is deposited over a layer of an adhesion promoting material.

28. The method of claim 15, wherein the support is a glass plate or a glass slide.

29. The method of claim 15, wherein the uniformity in the orientation of the liquid crystal disposed on the self-assembled monolayer increases after the device is contacted with the sample when the sample includes the compound.

30. The method of claim 15, wherein the compound that the functional group of the alkanethiol interacts with is an amine.

31. The method of claim 30, wherein the amine is an alkylamine.

32. The method of claim 31, wherein the alkylamine has the formula $H_2N(CH_2)_mCH_3$, wherein m has a value of 0, 1, 2, 3, 4, 5, 6, 7, 8, 9, or 10.

33. The method of claim 32, wherein the alkylamine is hexylamine.

34. The method of claim 30, wherein the amine is a biogenic amine.

35. The method of claim 34, wherein the biogenic amine is selected from the group consisting of histamine, putrescine, and cadaverine.

36. The method of claim 15, wherein the compound that the functional group of the alkanethiol interacts with is a phosphorus compound.

37. The method of claim 36, wherein the phosphorus compound is an organophosphonate.

38. The method of claim 37, wherein the organophosphonate is a dialkyl alkylphosphonate.

39. The method of claim 38, wherein the dialkyl alkylphosphonate is dimethyl methylphosphonate.

40. The method of claim 15, wherein the sample is a gaseous sample or a liquid sample.

41. The method of claim 15, wherein the device for detecting the presence of a compound in a sample is a component of an optical cell comprising a second surface that uniformly aligns the liquid crystal when the liquid crystal contacts the second surface.

42. A kit for detecting the presence of a compound in a sample, comprising:
    (a) a substrate having a support with a metallized top surface;
    (b) an alkanethiol comprising a functional group that reversibly or irreversibly interacts with the compound, wherein the functional group comprises a metal selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu; and
    (c) a liquid crystal having a moiety that interacts with the functional group of the alkanethiol.

43. The kit of claim 42, wherein the functional group of the alkanethiol comprises a metal carboxylate.

44. A method for manufacturing a device for detecting the presence of a compound in a sample, comprising:
    (a) depositing a metal on a surface of a support to form a support with a metallized surface;
    (b) contacting an alkanethiol with the metallized surface of the support to form a self-assembled monolayer with a bottom surface attached to the metallized top surface of the support and a top surface, wherein the alkanethiol includes a functional group that reversibly or irreversibly interacts with the compound;
    (c) contacting at least a first region of the self-assembled monolayer with a first metal salt to produce a first region with a first metal complex, wherein the metal is selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu; and
    (d) depositing a liquid crystal on the top surface of the self-assembled monolayer, wherein the liquid crystal comprises a moiety that interacts with the functional group of the alkanethiol.

45. The method of claim 44, wherein the functional group of the alkanethiol is a carboxylic acid.

46. The method of claim 44, wherein the first metal complex is a metal carboxylate.

47. The method of claim 44, wherein the liquid crystal comprises a nitrile group.

48. The method of claim 44, wherein the liquid crystal is 4-cyano-4'-pentylbiphenyl.

49. The method of claim 44, wherein the metal deposited on the support comprises gold and the gold is obliquely deposited on the support at an angle of from about 30° to about 60° to a top surface of the support.

50. The method of claim 49, wherein the gold is obliquely deposited on the support at an angle of about 50° to the top surface of the support.

51. The method of claim 49, wherein the gold is deposited over a layer of an adhesion promoting material on the surface of the support.

52. The method of claim 44, wherein the support comprises a glass plate or a glass slide.

53. The method of claim 44, further comprising positioning a second surface above the top surface of the self-assembled monolayer, wherein the second surface uniformly aligns the liquid crystal when the liquid crystal contacts the second surface.

54. The method of claim 53, wherein the second surface is a second support comprising a metallized surface having a second self-assembled monolayer comprising a second alkanethiol, wherein the second alkanethiol is different from the alkanethiol having the functional group that interacts with the compound.

55. The method of claim 44, further comprising contacting a second region of the self-assembled monolayer with a second metal salt different from that of the first metal salt to produce a second region of the self-assembled monolayer with a second metal complex that is distinct from the first region of the self-assembled monolayer.

56. A device for detecting the presence of a compound in a sample, comprising:
    (a) a surface including functional groups, wherein the functional groups are bonded to a metal forming a metal complex, wherein the metal is selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu; and
    (b) a liquid crystal deposited over the surface, the liquid crystal including a moiety that reversibly binds to the metal of the metal complex such that at least a portion of the liquid crystal is bound to the metal complex;
    wherein the metal complex is capable of reversibly or irreversibly binding a portion of the compound to be detected, such that when the compound is present in the sample, the portion of the compound will interact with the metal complex and displace at least some of the liquid crystal that was bound to the metal complex.

57. The device of claim 56, wherein the moiety of the liquid crystal is a nitrile group.

58. The device of claim 56, wherein the surface including functional groups comprises a semiconductor-based material and a self-assembled monolayer formed from alkanethiols bearing the functional groups.

59. The device of claim 58, wherein the semiconductor-based material is gallium arsenide.

60. A method for manufacturing a device for detecting the presence of a compound in a sample, comprising:
    (a) depositing a metal on a surface of a support to form a support with a metallized surface;
    (b) contacting an alkanethiol with the metallized surface of the support to form a self-assembled monolayer with a bottom surface attached to the metallized top surface of the support and a top surface, wherein the alkanethiol includes a functional group that reversibly or irreversibly interacts with the compound; and
    (c) contacting a first region of the self-assembled monolayer with a first metal salt to produce a first region with a first metal complex and contacting a second region of the self-assembled monolayer with a second metal salt different from that of the first metal salt to produce a second region of the self-assembled monolayer with a second metal complex that is distinct from the first region of the self-assembled monolayer; and (d) depositing a liquid crystal on the top surface of the self-assembled monolayer, wherein the liquid crystal comprises a moiety that interacts with the functional group of the alkanethiol.

61. The device of claim 60, wherein the second metal complex is a $Cd^{+2}$ carboxylate.

62. A device for detecting the presence of a compound in a sample, comprising:
 (a) a surface including functional groups, wherein the functional groups are bonded to a first metal in a first region forming a first metal complex and the functional groups are bonded to at least a second different metal in at least a second region of the surface forming at least a second metal complex; and
 (b) a liquid crystal deposited over the surface, the liquid crystal including a moiety that reversibly binds to the metal of at least the first metal complex such that at least a portion of the liquid crystal is bound to the first metal complex;
 wherein at least the first metal complex is capable of reversibly or irreversibly binding a portion of the compound to be detected, such that when the compound is present in the sample, the portion of the compound will interact with at least the first metal complex and displace at least some of the liquid crystal that was bound to the first metal complex.

63. The device of claim 62, wherein the first metal complex is a $Cu^{+2}$ complex.

64. The device of claim 62, wherein the second metal complex comprises a metal selected from the group consisting of Cd, Rb, K, Li, Cs, Ag, Au, Zn, Ti, Cr, Mn, Fe, Co, Ni, Zr, Nb, Ru, Rh, Hf, Ta, Re, Os, Ir, Pt, La, Sn, and Eu.

65. The device of claim 62, wherein the second metal complex is a $Cd^{+2}$ carboxylate.

66. The device of claim 62, wherein the surface including functional groups comprises a semiconductor-based material and a self-assembled monolayer formed from alkanethiols bearing the functional groups.

67. The device of claim 66, wherein the semiconductor-based material is gallium arsenide.

* * * * *